(12) United States Patent
Shriver

(10) Patent No.: US 8,702,730 B2
(45) Date of Patent: Apr. 22, 2014

(54) INTRAVASCULAR SUTURING DEVICE FOR SIMULTANEOUSLY PLACING 3-7 SUTURES WITH IDEAL SPACING TO CLOSE LARGE OPENINGS IN VESSELS INCLUDING CALFIFIED

(76) Inventor: Edgar Louis Shriver, Aventura, FL (US)

(*) Notice: Subject to any disclaimer, the term of this patent is extended or adjusted under 35 U.S.C. 154(b) by 0 days.

(21) Appl. No.: 13/374,779

(22) Filed: Jan. 11, 2012

(65) Prior Publication Data
US 2013/0178872 A1 Jul. 11, 2013

(51) Int. Cl.
*A61B 17/04* (2006.01)

(52) U.S. Cl.
USPC .......................... 606/144; 606/148

(58) Field of Classification Search
USPC ............... 606/139, 144, 145, 148, 147
See application file for complete search history.

(56) References Cited

U.S. PATENT DOCUMENTS

| | | | | |
|---|---|---|---|---|
| 2,264,679 A | * | 12/1941 | Ravel | 606/144 |
| 5,470,338 A | * | 11/1995 | Whitfield et al. | 606/144 |
| 5,653,717 A | * | 8/1997 | Ko et al. | 606/144 |
| 5,700,273 A | * | 12/1997 | Buelna et al. | 606/148 |
| 5,836,956 A | * | 11/1998 | Buelna et al. | 606/148 |
| 6,245,079 B1 | * | 6/2001 | Nobles et al. | 606/144 |
| 6,613,058 B1 | * | 9/2003 | Goldin | 606/144 |
| 7,722,629 B2 | * | 5/2010 | Chambers | 606/144 |
| 8,123,764 B2 | * | 2/2012 | Meade et al. | 606/145 |
| 8,409,224 B2 | * | 4/2013 | Shriver | 606/144 |

* cited by examiner

*Primary Examiner* — Dianne Dornbusch
*Assistant Examiner* — Robert Lynch

(57) ABSTRACT

A centerboard shaped like a long board has width that spreads a vessel opening to a slit with free edges drawn against centerboard. Needle pairs are two shafts temporarily attached to needle noses located in openings at 2 mm intervals across centerboard width. Pushing a wedge between pairs spreads needle noses about 1 mm on either side of centerboard. Suture loops ends are attached to needle noses of each pair. An outboard has legs like long boards on either side of the centerboard with a foot on each leg pointing away from centerboard on either side of slit outside vessel. Needle nose housings in each foot are directly opposite needle noses. Operator turning a screw pushes needle noses through free edges and into needle nose housings where detents hold needle noses and shafts detach. Removing device from body brings suture ends outside with suture loops across slit in ideal 2×2 pattern.

9 Claims, 7 Drawing Sheets

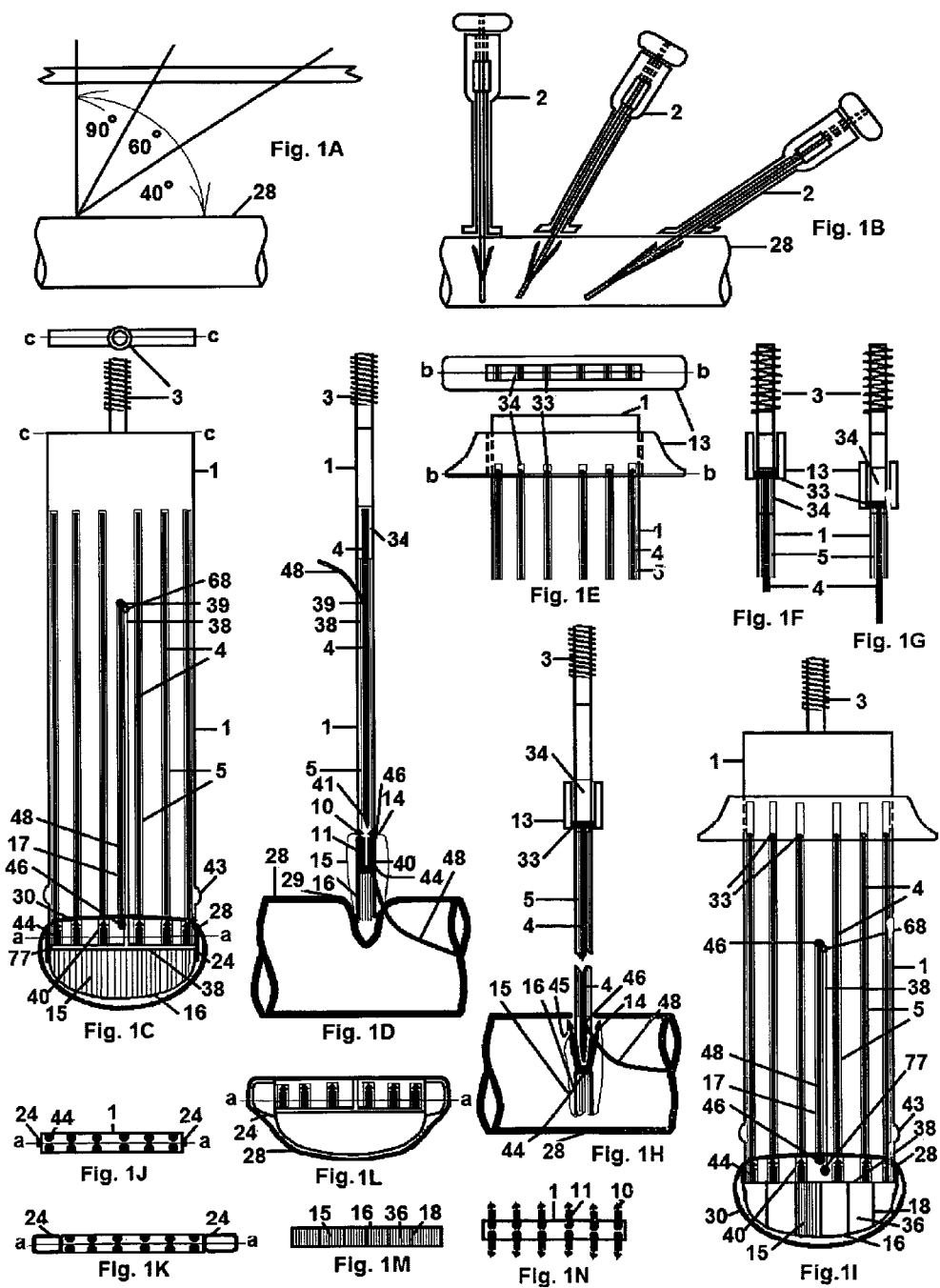

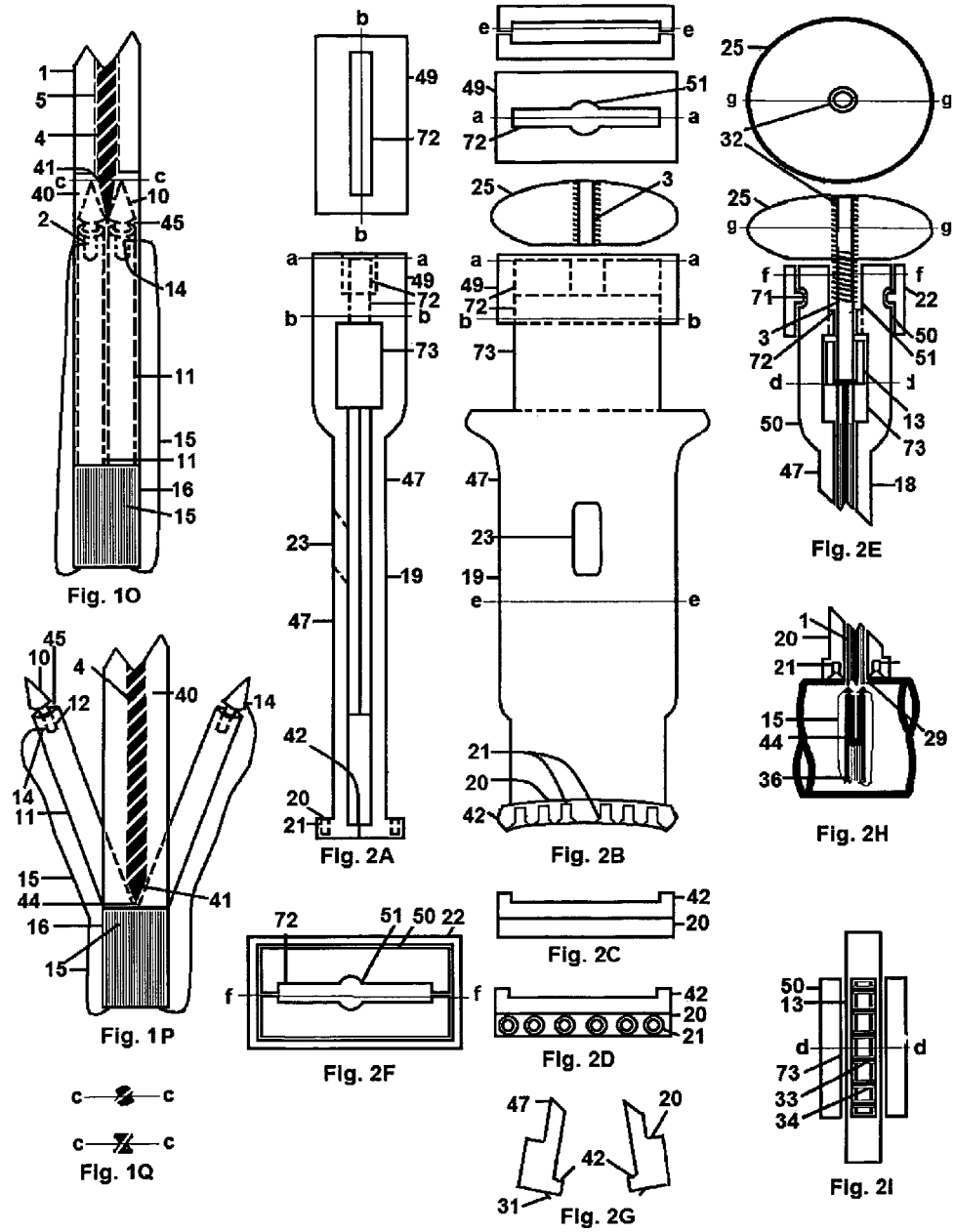

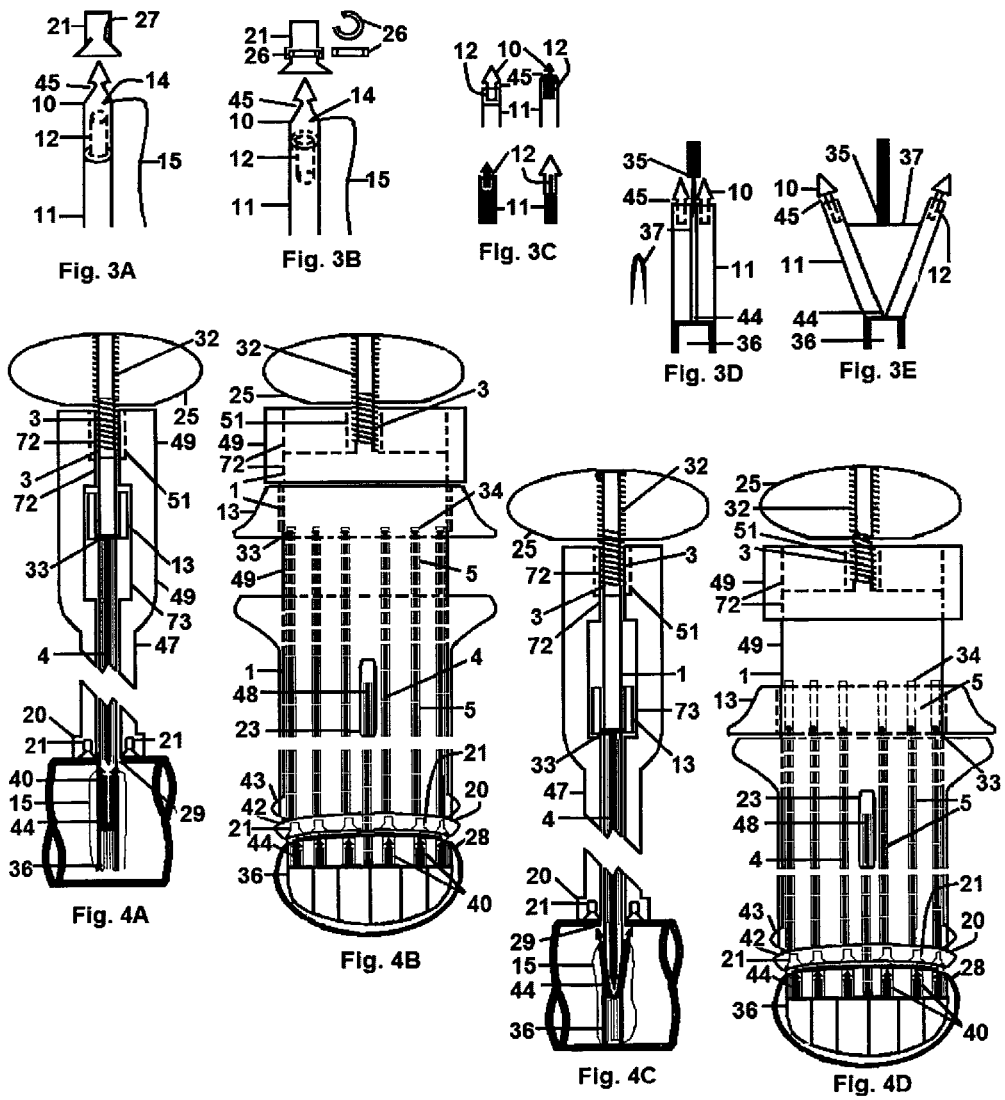

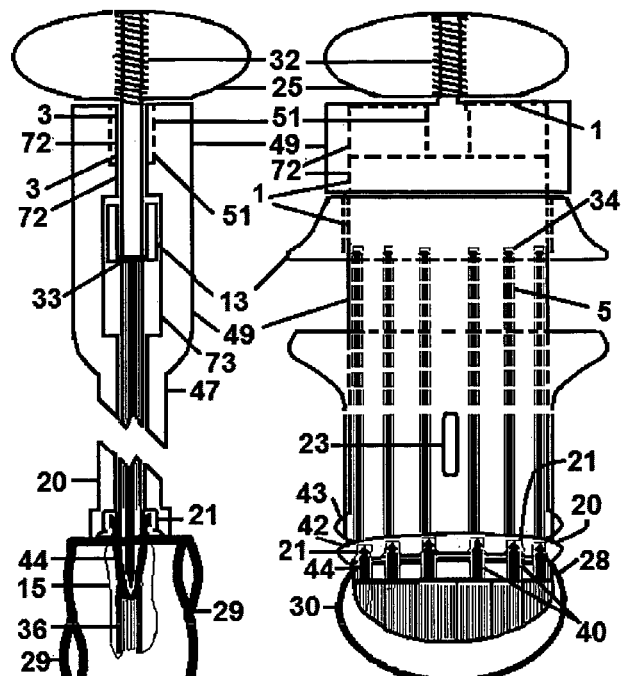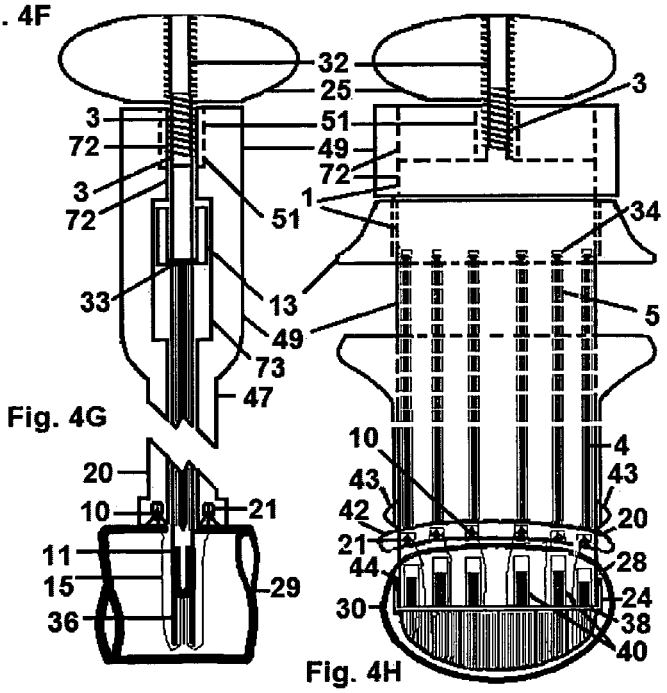

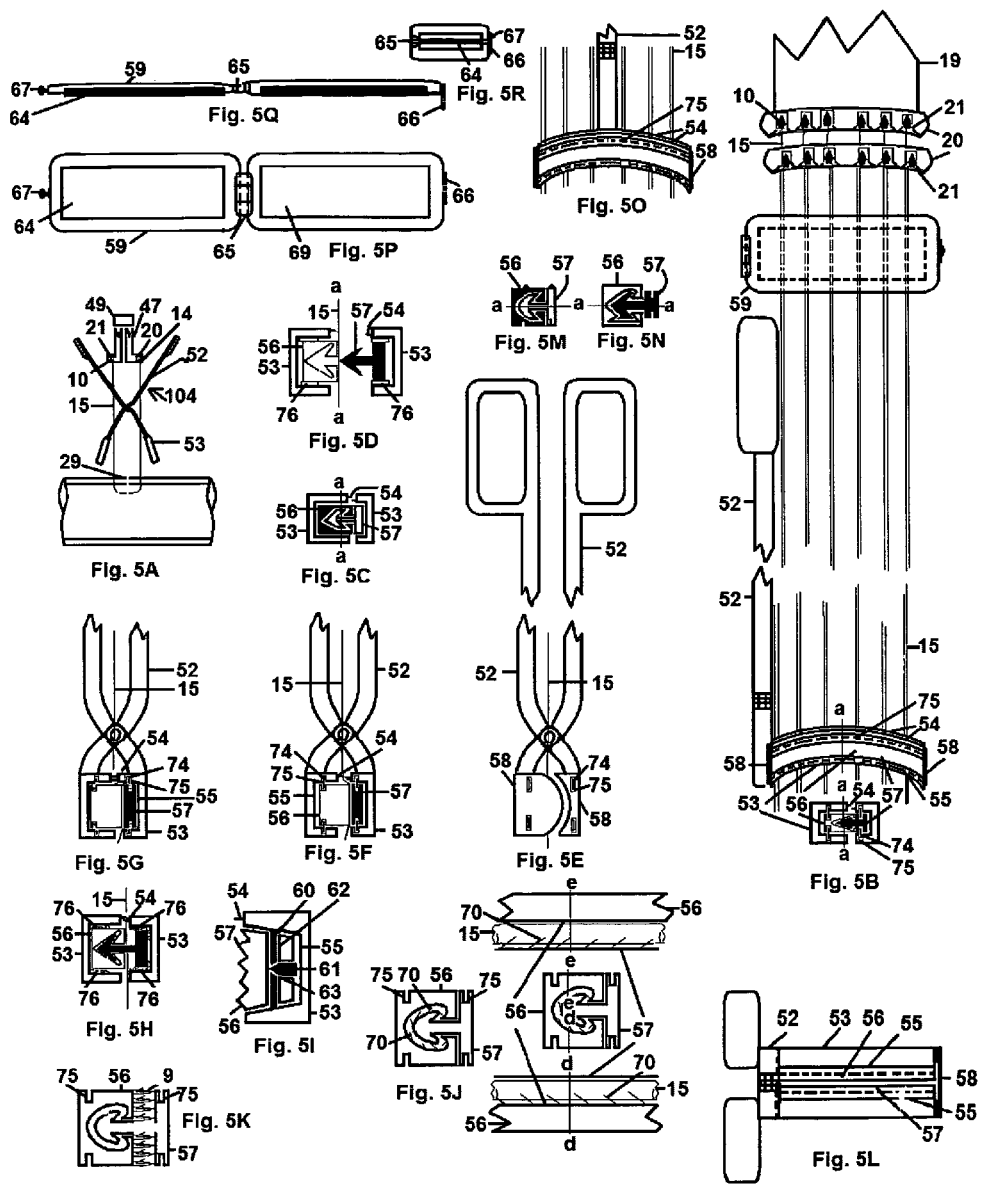

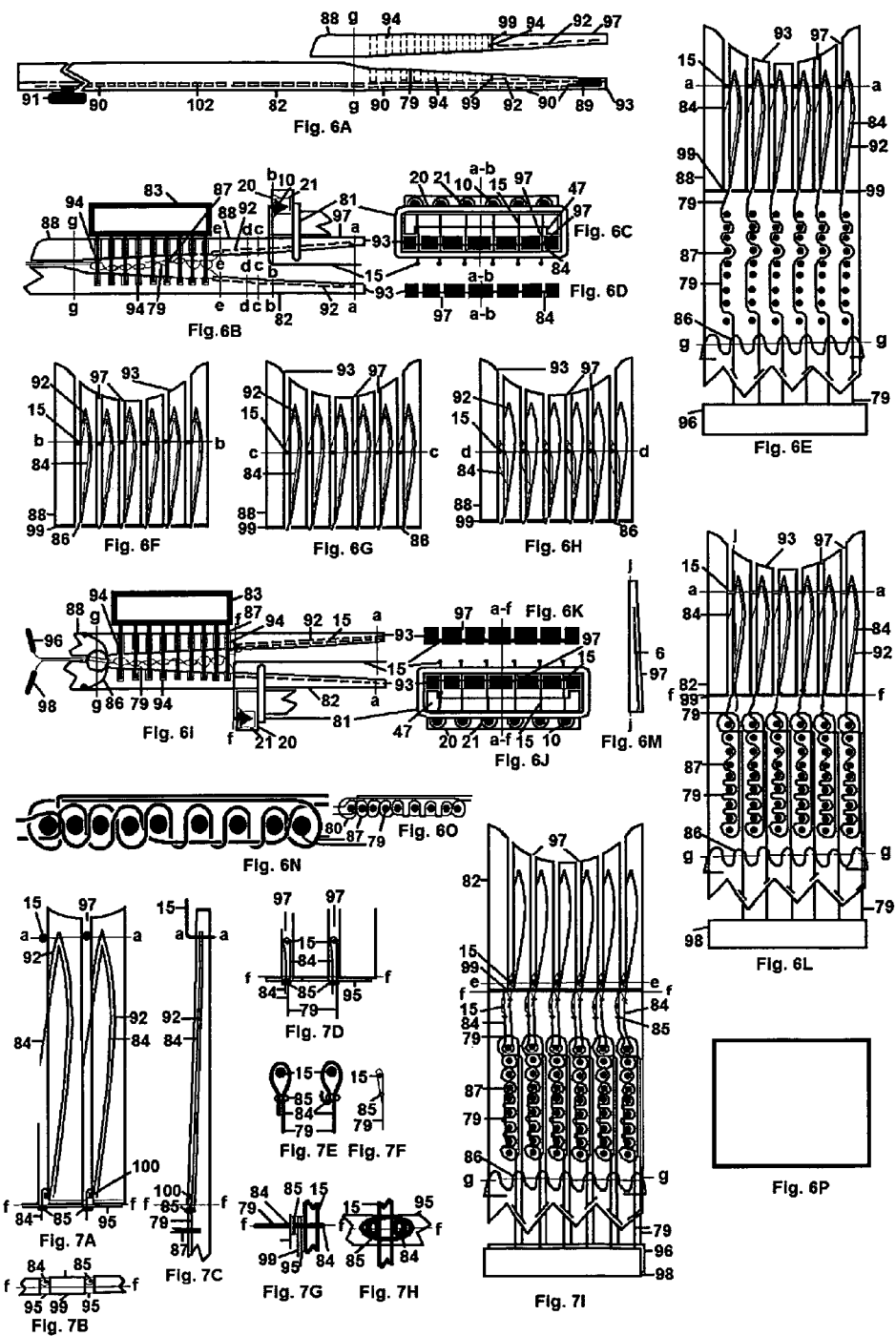

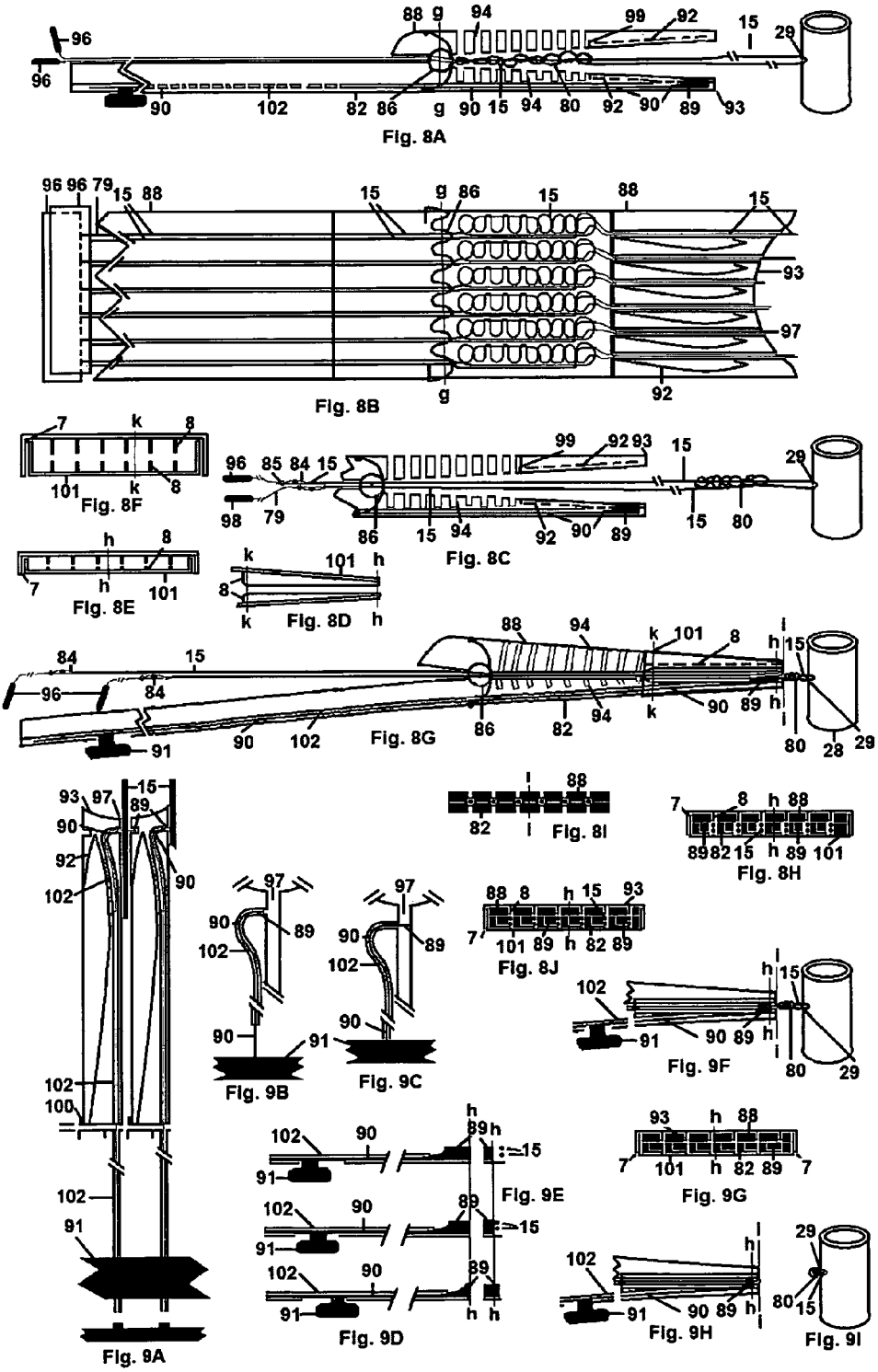

INTRAVASCULAR SUTURING DEVICE FOR SIMULTANEOUSLY PLACING 3-7 SUTURES WITH IDEAL SPACING TO CLOSE LARGE OPENINGS IN VESSELS INCLUDING CALFIFIED

CROSS-REFERENCE TO RELATED APPLICATIONS

This is a new invention by the inventor of vascular devices disclosed in U.S. Pat. No. 7,771,442, U.S. Pat. No. 7,959,644, and U.S. Pat. No. 7,713,215, that require relatively large percutaneous openings in arteries for device entry; the object of the present patent application being to percutaneously close large openings such as 9 F to 32 F in vascular vessels; including calcified, with an ideal curved line of sutures placed simultaneously without tying and placing knots individually.

FEDERALLY SPONSORED RESEARCH

Not Applicable

SEQUENCE LISTING OR PROGRAM

Not Applicable

BACKGROUND OF THE INVENTION

1. Field of the Invention

The field generally relates to vascular closure devices that use plugs, mechanical pressure, or sutures to close percutaneous openings of size 3-10 F. Specifically, the present device provides a means for simultaneously placing an ideal pattern of sutures in a vascular vessel that may be calcified to close openings such as 9-32 F without surgery now required to achieve this object.

2. Prior Art

| | | |
|---|---|---|
| 3,470,875 | October 1969 | Johnson |
| 3,665,926 | May 1972 | Flores |
| 4,161,951 | July 1979 | Scanlon Jr. |
| 4,553,543 | November 1985 | Amarasinghe |
| 4,587,969 | May 1986 | Gillis |
| 4,744,364 | May1988 | Kensey |
| 4,852,568 | August 1989 | Kensey |
| 4,890,612 | January 1990 | Kensey |
| 4,929,246 | May 1990 | Sinofsky |
| 5,021,059 | June 1991 | Kensey, et al |
| 5,049,138 | September 1991 | Chevalier |
| 5,059,201 | October1991 | Asnis |
| 5,061,274 | October 1991 | Kensey |
| 5,087,263 | February 1992 | Li |
| 5,160,339 | November 1992 | Chen, et al |
| 5,163,946 | November 1992 | Li |
| 5,217,470 | June 1993 | Weston |
| 5,171,251 | December 1992 | Bregen, et al |
| 5,383,896 | Jan 1995 | Gershony |
| 5,411,481 | May 1995 | Allen, et al |
| 5,454,820 | October 1995 | Kammerer, et al |
| 5,454,821 | October 1995 | Harm, et al |
| 5,613,974 | Mar 25 1997 | Andreas et al |
| 5,728,109 | March 1998 | Shultz, et al |
| 5,769,862 | June 1998 | Kammerer, et al |
| 5,776,150 | July 1998 | Nolan, et al |
| 5,814,069 | September 1998 | Shultz, et al |
| 6,090,130 | Jul. 18, 2000 | Nash et al |
| 7,713,215 | May 11 2010 | Shriver |
| 7,771,422 | Aug. 10, 2010 | Shriver |
| 7,959,644 | Jun. 14, 2011 | Shriver |

3. Devices and Procedures

Millions of percutaneous endovascular interventional procedures are performed each year to treat diseased coronary and peripheral arteries. The percutaneous method for entering arteries was described by Seldinger: the skin is punctured with a hollow needle pushed through a layer of subcutaneous adipose (fat) tissue to puncture an artery, usually the common femoral artery (CFA) in the groin. The angle of entry is generally between 40 degrees and 60 degrees. A guidewire is then advanced through the hollow needle to enter the artery lumen. The hollow needle is withdrawn and an introducer sheath advanced over the guidewire into the opening, thus forcing the opening to the size of the sheath. Introducer sheath has proximal end outside the body and distal end inside the artery lumen and a circumference large enough to introduce the size of tools and graft materials needed for the intended procedure on arteries of the heart or peripheral to the heart, e.g. in legs or neck. The opening forced by the sheath splits the artery from side to side rather than along the longitudinal axis. Since openings in the body are not perfect circles the French measurement system approximates the circumference of the opening's free edge in mm by expressing diameter in units that are $\frac{1}{3}$ mm. Thus an opening, sheath, or catheter that is 1 French (1 F) is $\frac{1}{3}^{rd}$ mm in diameter and approximately 1 mm in circumference, and 3 F is 1 mm in diameter and about 3 mm (an approximation of 3.14 mm) in circumference. Fluid pressure in the introducer sheath is maintained at a level that prevents blood pressure in the artery from causing blood to flow from the artery through the opening. When the procedure is finished tools and sheath must be removed and the opening closed.

The Seldinger method of closing is used for small openings such as 3 F. Pressure is applied manually on the skin opposite the opening after removing the sheath. The manual pressure must be greater than the blood pressure within the artery in order to maintain hemostasis while the natural elasticity of the blood vessel wall reduces the size of the opening until, after sufficient reduction, a blood dot forms to finally close the opening. The natural recoil of the vessel wall free edge around the opening might require 15 minutes of manual pressure for a 3 F opening but hours for an opening such as 6-8 F. And in older people the elasticity of vessel wall is less and thus recoil takes longer. Disadvantages of the pressure method include time and discomfort of patient but the advantage is minimal complications. Thus manual pressure is still the gold standard for access site management but the disadvantage of time required to ambulation has led to the evolution of many alternatives. None of these alternatives apply to openings larger than 8 F as the present invention does, so this background is only generally relevant to the present invention.

Mechanical Pressure

A certain type of device applies mechanical pressure to reduce the size of a larger opening to a smaller opening that can finally be closed by manual pressure. This type of device requires manual pressure to make the final closure because a wire or tube remains in the path left by the sheath when it was removed and the opening cannot close until it is removed. These devices are not intended for use with openings larger than 6-8 F. Gershony in U.S. Pat. No. 5,383,896 reveals a balloon on a tube that is preferably not greater than 0.038 inches in outside diameter. The tube is advanced through the sheath so the balloon on the distal end can be inflated in the artery lumen. The balloon is pre-selected to be larger than the opening so it blocks blood and maintains hemostasis after the sheath is removed. A relatively large diameter fixation collar is located on the proximal end of the tube (shaft) and pressed against the skin opposite the opening to allow its place to be secure within the blood vessel. Another device for applying mechanical pressure is available under the commercial name Boomerang™. It utilizes site-specific compression, similar to that of the Gershony device. But instead of a balloon in the vessel lumen, this device has a collapsible wire mesh disc on the end of a wire. The collapsed disc is pushed through the sheath by the wire and adjusted into a flat disc inside the lumen. The flat wire disc is larger than the opening but is somewhat porous so does not seal the opening to achieve hemostasis. Hemostasis is achieved after the sheath is removed by clipping a detent on the wire against the skin where manual pressure is normally applied. The pressure can be adjusted by moving the detent more firmly against the skin—as manual pressure from a finger would be applied. This may be done in the cath lab in less than a minute to produce hemostasis. The patient can then be moved from the cath lab with the device in place. The opening relaxes around the wire by the natural process of elastic recoil while normal clotting mechanisms begin. The natural elastic recoil of the vessel wall occurs unless the patient's artery has lost so much elasticity that it does not fully recoil. When the size of the opening has reduced to the size of the wire, the wire disc is collapsed and the device removed. Normal manual pressure is then applied to close the remaining opening left by the removed wire.

Sealants/Plugs

There are a number of patented vascular closure devices (VCD) for placing a sealant or plug in the opening or in adjacent fat tissue with some success in the market. The invention revealed by Kensey in 4890612 describes the type of device that creates a plug for the opening. A relatively hard anchor disc is attached to a filament (string) introduced through an elongated tube with a plunger. This places the anchor disc in the artery lumen and the string is used to pull the plug against the opening while a biodegradable gel foam or collagen is pushed through the tube to surround the string and fill the opening. This maintains hemostasis and the plug biodegrades within a month or two. This device is handicapped by two properties inherent to the technology. First, the anchor placed inside is occasionally obstructive, either at the puncture site or with embolization. Second, it leaves a mass of collagen inside the tissue track and a filament (string) that extends from the arteriotomy to near the skin surface, which provides both a nidus and a wick for potential infection. There are other devices for placing plugs of this type without a string, e.g. Angio-Seal, a commercial device similar to the Kensey device still leaves a thrombosing agent in the tissue track. Another plug-type device uses a balloon as an alternative form of anchor disc. The balloon is opened in the lumen and held against the opening while the biodegradable seal substance is injected to plug the opening. There are also various patches to place on the skin and chemical gels applied under the skin to counteract the effects of anticoagulants used during many percutaneous procedures to prevent clotting. These must be reversed when clotting is needed to close the opening. There are several reasons these VCDs have not displaced the simple pressure method to meet the need for a rapid, safe, and reliable hemostasis. They have not clearly been shown to reduce the incidence of bleeding, vascular complications or cost when compared with traditional compression but have been successful in decreasing time to ambulation. Obese patients are among the best candidates for these alternatives because direct pressure on the skin of an obese person may be transmitted laterally through fat layers and away from the opening, thus providing insufficient pressure at the vessel. These devices are used for closing openings up to 6 F.

Staples/Clips

Another type of closure device uses staples or clips to close the opening. The device called Starclose® advances a ring of barbs through the sheath and into the edge around the opening. The barbs are then turned inward to clip together the edge and thus close the opening. No manual compression is needed after using this device as it closes small openings completely. This device is not intended for use with large openings, there is relatively little experience with it and it is not in common use.

Intravascular Sutures

During the few minutes a suture is being placed, blood is stopped from flowing in the artery by applying pressure on the skin opposite. After a suture closes the opening, the suture provides hemostasis; there is no requirement for further pressure, sealants or lengthy time to ambulation. Other types of devices for maintaining hemostasis without sutures were briefly reviewed as general background. But there is only one device for closing percutaneous openings by a suture and it places one suture. It is based on U.S. Pat. No. 5,613,974 of Mar. 25, 1997 by Andreas et al, which is assigned to Perclose®, now owned by Abbott labs, and describes a type of intravascular suture closure device approved for placing one suture in an opening up to 8 F. That invention and those prior to it are included as potential prior art for the present invention of an intravascular suturing device that places a plurality of sutures in a particular ideal pattern. A common femoral artery is about 1 mm thick at an opening made for percutaneous procedures and an opening of 8 F is a little more than 8 mm in circumference. The free edge of that circumference folds to a slit of a about half the circumference, or 4+ mm. Placing one suture across the free edge leaves about 2 mm on each side. When a surgeon has free access to place sutures, he/she will place the needle at a distance from the free edge that is equal to the thickness of the artery and place successive sutures twice this distance apart. Thus the Perclose device does this for openings up to 8 mm in circumference of 8 F, and that is the largest opening for which the device is approved for use.

Ideal Spacing of Sutures

The ideal spacing of sutures is 2 mm between sutures and 2 mm across free edge for an artery with wall thickness of 1 mm. Thus two sutures in the ideal pattern will close a slit of 6 mm (2 mm on each side and 2 mm between 2 sutures), 3 sutures will be required for a 8 mm slit, 4 for a 10 mm slit, 5 for a 12 mm, etc. A 24 F opening is about 24 mm in circumference so closes to a 12 mm slit that require 5 sutures 2 mm apart. The suturing pattern described as "ideal" is the result of numerous studies with animals and practice with human patients. There is a tendency for the lumen to be reduced along the line of suture across the artery. This reduction can be avoided by placing sutures 2 mm apart and 1 mm from the free edges of the slit with vessel wall thickness of 1 mm. This creates a slight increase in mass of tissue edges in opposition across each suture that exerts lateral pressure that counteracts the tendency to constrict the lumen, thus producing a curved line of sutures matching the original curvature of the vessel. This curved line of sutures is called a two-by-two as each puncture site is 2 mm from the one opposite it across the free edge and 2 mm from the adjacent. For a vein with thinner wall the distances should be closer to 3 by 3 mm. Vessel walls vary in both thickness and diameter among individuals but on average common femoral arteries (the usual site of percutaneous entry) are about 1 mm thick and about 7 to 11 mm in diameter, making artery circumference range from about 22 mm to 33 mm.

Larger Openings Required

There are procedures requiring openings of 24 F or even larger, e.g. aneurysms of the larger arteries of the legs such as abdominal aortic arch and of carotid arteries. Cut down for a surgeon to place sutures to close large opening has traditionally been used after these procedures so the surgeon can apply the ideal number and spacing of sutures manually. However open surgery has its own disadvantages and risks, so some exceptions are made to allow off-label use of a Prostar XL® device or two Perclose® devices to make a "purse-string" closure of the opening, pulling four points on the edge of the opening to the center and thus producing a closure that is not ideal, is technically difficult to perform, has some complications, and is usable only under certain conditions. Making the appropriate knot to tie suture ends also requires considerable skill and time so if alternative means can be invented to join suture ends by a faster, safer way than tying a knot in each, that would be an added advantage. Thus "off-label" is a workable solution for highly skilled practitioners but not a satisfactory long-term general solution for routinely closing large openings.

Device Characteristics for Meeting Future Needs

In addition to procedures that now require large openings, there are new procedures for replacing heart valves through large percutaneous openings, such as 24 F. These require highly skilled practitioners now but if they are to become generally usable a better means than off-label use of devices will be needed. And if devices for placing bypass grafts around occluded arteries of the heart and legs are to replace the less effective angioplasty devices that use balloons and stents, an effective, safe and easily performed means of closing the required large openings will be required. An approved device for closing larger openings by sutures that meet the ideal spacing criterion of surgically placed sutures would be preferred over a purse string pattern. Another problem of placing sutures in arteries is that they are frequently calcified making it difficult to push a suturing needle through the vessel wall even when the surgeon can manually access the artery. If a device can provide means for pushing needles through calcified arteries more effectively than a surgeon can manually, that would be still another advantage. And if sutures can be placed simultaneously rather than sequentially as required with manual suturing and other devices, that is another major advantage by reducing time to perform. If the new device were to use pre-tied knots it would eliminate a difficult step reducing both the time and skill required. The availability of a device with any or all of these desired characteristics could be an important determinant of what type of other devices become practical for accomplishing future procedures such as transcatheter aortic valve implantation and transcatheter bypass graft placement. The present invention is expected to have all these advantages with its initial application being to closing large openings in common femoral arteries after completion of a percutaneous procedure requiring a large opening. It also applies to other vessels such as veins and even to skin, but the example used will be an artery in order to simplify the discussion. The device is designed as a means of placing sutures in the ideal 2×2 pattern in a curved line, provide means for penetrating calcified arteries with greater ease than a surgeon can achieve manually, place all sutures simultaneously with easily performed steps, and provide a quickly applied simple alternative to manual knot tying each knot individually and cutting all ends at opening simultaneously.

Advantages

1. Millions of procedures are performed each year that require percutaneous openings of 3-6 F. Manual pressure is commonly used for closing openings of 3 F and there are numerous devices for closing openings up to 6 F, generally by plugging the opening with substances that are foreign to the body and thus not desirable. There are two devices for closing opening up to 8-10 F by placing one or two sutures in a cross pattern to make a purse string closure which has disadvantages with respect to ideal suture closures made with open surgery.

2. The Perclose® device is approved for placing one suture to close opening up to 8 F. The Prostar XL® device is approved for placing two sutures in a cross pattern for a purse string closure of openings up to 8-10 F. Open surgery places any number of sutures in the ideal pattern of 2×2 to close openings of 24 F or even larger, but has the disadvantage of more risk and greater trauma have devices for closing openings percutaneously.

3. The only currently approved means of closing openings of 11 to 24 F is with sutures manually placed by a surgeon, and this is done in the ideal configuration of sutures being 2 mm apart and 2 mm across the free edge of the slit produced by drawing the opening to half its circumference. It is called 2×2 and is ideal because it produces a curved line of sutures that matches the original vessel shape thus not narrowing the vessel. For veins of less than 1 mm thickness a distance of 3 mm apart and 3 mm across free edge is ideal, and called 3×3. There are increasing numbers of procedures that require larger openings and no device is approved for percutaneously closing openings larger than 8-10 F.

4. To avoid the risks and debilitation of open surgery for closing openings larger than 10 F, physicians sometimes use one Prostar XL® device with an unapproved technique or two Perclose® devices, also off-label, to place two sutures in a cross pattern thus making purse string closures of openings up to 24 F—or even larger. This off label use of devices is technically difficult, does not prevent narrowing the vessel, is done only under restricted conditions, and has other complications, so cannot be long-term solutions for closing openings larger than 8-10 F.

5. The intravascular suturing device described and claimed herein is appropriate for percutaneously closing openings of 6-33 F with the ideal configuration of 2 to 7 sutures in a curved line that avoids narrowing the vessel. Thus the device avoids the risks of surgery while achieving the ideal suturing configuration and has other important advantages.

6. The device claimed herein places sutures simultaneously rather than sequentially. A skilled surgeon requires more than a minute to place one suture, or about the time required by the device to place all sutures. The other devices require even more than a minute to place each of two sutures in a cross pattern.

7. Another problem with placing sutures is the skill and time required to tie the ends of each suture with a special knot, run them individually to vessel wall and cut each with a special tool. The present intravascular suturing device provides preformed knots or clips to secure suture ends, runs knots to vessel wall and cuts knot ends at vessel wall simultaneously.

8. Still another problem with placing sutures is that arteries and veins are frequently calcified making it difficult to push a suturing needle through the wall and the wall stretches in the direction of applied needle force. The surgeon can't place a finger in front of the needle to prevent the stretching and has no other means of counteracting this tendency. The present device provides a needle housing outside the calcified vessel wall opposite the needle nose inside the vessel wall and they are forced together with the force of an inclined plane thereby piercing the calcified vessel wall between.

9. The advantages of this device are that it does not require surgery, closes large openings that other vascular closure devices cannot close or close less effectively, places sutures simultaneously in less time than other means and accomplishes this in calcified or non-calcified vessels in less time, more effectively and without the risks of manual suturing.

| Key | | |
|---|---|---|
| 1. | | Center board |
| 2. | | Suture placement component |
| 3. | | Threaded post |
| 4. | | Separator wire |
| 5. | | Separator wire channel |
| 6. | | Short snare groove |
| 7. | | Overlap |
| 8. | | Slot stopper |
| 9. | | Loops and hooks |
| 10. | | Needle nose |
| 11. | | Needle shaft |
| 12. | | Friction dowel |
| 13. | | Frame |
| 14. | | Suture end |
| 15. | | Suture loop |
| 16. | | Suture cove |
| 17. | | Guidewire channel |
| 18. | | Cove wall |
| 19. | | Outboard |
| 20. | | Foot |
| 21. | | Needle nose housing |
| 22. | | Surround |
| 23. | | Access slot |
| 24. | | Balloon |
| 25. | | Screw turner |
| 26. | | Spring clip |
| 27. | | Housing detent |
| 28. | | Vessel wall |
| 29. | | Free edge slit side |
| 30. | | Free edge slit across |
| 31. | | Spur |
| 32. | | Female threads |
| 33. | | Cross wire |
| 34. | | Cross slot |
| 35. | | Blunt end |
| 36. | | Suture compartment |
| 37. | | Bridge wire |
| 38. | | Fluid channel |
| 39. | | Proximal port |
| 40. | | Needle opening |
| 41. | | Wedge end |
| 42. | | Keeper |
| 43. | | Stopper |
| 44. | | Needle pair |
| 45. | | Nose indent |
| 46. | | Distal port |
| 47. | | Outboard legs |
| 48. | | Guidewire |
| 49. | | Blockhead |
| 50. | | Split blockhead |
| 51. | | Unthreaded hole |
| 52. | | Cross clamp |
| 53. | | Crossbar |
| 54. | | Scissors cutter |
| 55. | | Strip holder |
| 56. | | Female strip |
| 57. | | Male strip |
| 58. | | Suture shield |
| 59. | | Tension adjustor |
| 60. | | Slant end rod |
| 61. | | Release rod |
| 62. | | Slant channel |
| 63. | | Release channel |
| 64. | | Friction pad |
| 65. | | Hinge |
| 66. | | Clasp |
| 67. | | Clasp button |
| 68. | | Fluid port proximal |
| 69. | | Recessed area |

-continued

| Key | | |
|---|---|---|
| 70. | | Barbs |
| 71. | | Tongue and groove |
| 72. | | Centerboard slot |
| 73. | | Frame slot |
| 74. | | Break away strip |
| 75. | | Holder slot |
| 76. | | Compression breaker |
| 77. | | Fluid port distal |
| 78. | | Fluid port edge |
| 79. | | Knot leader |
| 80. | | Slip knot |
| 81. | | Foot loop |
| 82. | | Long applicator |
| 83. | | Knot rod holder |
| 84. | | Wire snare |
| 85. | | Snare tightener |
| 86. | | Spring roller |
| 87. | | Knot rods |
| 88. | | Short applicator |
| 89. | | Cutter end |
| 90. | | Cutter pusher |
| 91. | | Push knob |
| 92. | | Snare holder |
| 93. | | Applicator nose |
| 94. | | Knot rod channels |
| 95. | | Resistance film |
| 96. | | Rail leader board |
| 97. | | Suture slots |
| 98. | | Loop leader board |
| 99. | | Tightener gate |
| 100. | | Snare detent |
| 101. | | Pinch sleeve |
| 102. | | Cutter channel |
| 103. | | Suture tying component |
| 104. | | Suture clip component |

BRIEF DESCRIPTION OF THE DRAWINGS

FIG. 1A is a schematic representation of angles of percutaneous entry from skin to vessel wall with angles between 40 and 90 degrees.

FIG. 1B shows shapes suture placement component of the present specification would have for alternative angles of entry of 40, 60 and 90 degrees.

FIG. 1C is a plan view at cross section c and a cross sectional front view of centerboard with components. (Cross sectional views are used so components interior to the faces need not be shown as dashed lines).

FIG. 1D is a cross sectional side view of a centerboard with components.

FIG. 1E is a plan view at cross section b and a cross sectional front view of frame containing cross wires located near proximal end of cross slots.

1F is a cross sectional side view of frame before operator pushes it in the distal direction.

FIG. 1G is a cross sectional side view of frame after operator pushes it in the distal direction.

FIG. 1H is a cross sectional side view showing wedge end of separator wire between a needle pair after operator pushes frame in the distal direction.

FIG. 1I is a cross sectional front view of centerboard showing cross wires at distal end of cross slots after operator has pushed frame in distal direction.

FIG. 1J is a plan view of needle pairs and uninflated balloons at cross section a.

FIG. 1K is a plan view of needle pairs and inflated balloons at cross section a.

FIG. 1L is a frontal view of needles and inflated balloons inside vessel wall at cross section a.

FIG. 1M is a plan view of the distal end of centerboard with sutures in compartments.

FIG. 1N shows plan view of distal end of centerboard with needle pairs pushed apart.

FIG. 1O is a detail cross sectional side view of a needle pair in needle opening before wedge end of separator wire has been pushed between the pair.

FIG. 1P is a cross sectional side view of a needle pair after wedge end of separator wire has been moved distally to force needle pairs about 2 mm apart.

FIG. 1Q shows plan view of alternative configurations of wedge ends with sides curved to fit needle shafts at cross section c.

FIG. 2A is a side view of outboard with plan view at cross section b.

FIG. 2B is a frontal view of outboard and screw turner with plan views at cross sections a and e.

FIG. 2C is a plan view of a foot looking distally showing keepers

FIG. 2D is a plan view of a foot with keepers looking proximally showing open ends of needle nose housings.

FIG. 2E is a cross sectional side view of screw turner, proximal centerboard and outboard with split blockhead and surround plus a plan view at cross section g.

FIG. 2F is a plan view of split blockhead at cross section f.

FIG. 2G is a side view of outboard legs with each foot moved slightly apart and a spur on each foot.

FIG. 2H is a side view of distal portion of centerboard and outboard in free edge side slit before operator moves frame in distal direction.

FIG. 2I is a plan view of frame and cross wires between outboard legs at cross section d.

FIG. 3A is a cross sectional side view of needle shaft and nose with indent as held together by frictional dowel about to enter needle nose housing with detent.

FIG. 3B is a cross sectional side detail view of needle nose with spring clip indent as held to needle shaft by frictional dowel about to enter needle nose housing containing spring clip detent.

FIG. 3C shows four alternative configurations of friction dowels between needle shafts and noses.

FIG. 3D shows an alternate configuration for separating needle pairs by loop of bridge wire attached between a needle pair before separator wire has pushed bridge wire straight.

FIG. 3E shows needle pair pushed apart after separator wire pushes bridge wire straight.

FIG. 4A is a cross sectional side view of centerboard and outboard before operator pushes frame in distal direction.

FIG. 4B is a cross sectional frontal view of centerboard and outboard before operator pushes frame in distal direction.

FIG. 4C is a cross sectional side view of centerboard and outboard after operator pushes frame in the distal direction, pushing separator wedge between needle pairs.

FIG. 4D is a cross sectional frontal view of centerboard and outboard after operator pushes frame in distal direction, pushing separator wedge between needle pairs.

FIG. 4E is a cross sectional side view of centerboard and outboard after operator has turned screw turner to move needle noses through vessel wall and into needle housings.

FIG. 4F is a cross sectional frontal view of centerboard and outboard after operator has turned screw turner to move needle noses through vessel wall and into needle housings.

FIG. 4G is a cross sectional side view of centerboard and outboard after operator has turned screw turner in opposite direction leaving needle noses and suture ends in needle nose housings and needle shafts in centerboard.

FIG. 4H is a cross sectional front view of centerboard and outboard after operator has turned screw turner in opposite direction leaving needle noses and suture ends in needle nose housings and needle shafts in centerboard.

FIG. 5A shows a side view of a cross clamp open to collect suture loops running between free edge slit side and needle noses in the two feet of outboard legs.

FIG. 5B is a frontal view of the two feet and suture loops they hold running between cross clamp and tension adjustor, with cross sectional view at a-a showing male and female strips held by breakaway strips in strip holders.

FIG. 5C shows an alternative configuration of male and female strips in strip holders at cross section a, without compression breakers.

FIG. 5D shows an alternative configurations of male and female strips in strip holders at cross section a, with compression breakers.

FIG. 5E is a side view of cross clamp with the halves of suture shield on distal end that have holder slots through which breakaway strips are loaded.

FIG. 5F is the view of FIG. 5E with suture shield removed to show female and male strips held by breakaway strips. Strips have the same cross section at all points from apogee to perigee along curved crossbar so breakaway strips are shown without male and female strip shapes.

FIG. 5G is the same view as FIG. 5F with breakaway strips broken by cross clamp being partially closed.

FIG. 5H is the same view as FIG. 5G showing male and female strip shapes and an alternative configuration of compression breakers that turn into grains at their breaking tensile strength.

FIG. 5I is a cross section of strip holder and fragment representing female or male strip with slant end rod in slant channel and release rod in release channel.

FIG. 5J shows tiny barbs extending from the surface of male and female strips with one large scale and two small scale views of the same cross section as needed see how the tiny barbs are arranged on opposing surfaces.

FIG. 5K is an alternative configuration for preventing male strip from separating from female strip by attaching a plurality of hooks and loops to touching surfaces.

FIG. 5L is an end view of crossbars as viewed from the artery with suture shields on each end and male and female strips in strip holders.

FIG. 5M shows an alternative configuration of male and female strips.

FIG. 5N shows an alternative configuration of strips with sharp bends.

FIG. 5O shows cross clamp attached to middle of cross bar.

FIG. 5P shows plan view of a tension adjustor with friction pads.

FIG. 5Q is side view of an open tension adjustor with friction pads.

FIG. 5R is an end view of a closed tension adjustor with hinge.

FIG. 6A is a side view of short applicator and long applicator with components.

FIG. 6B is a side view of the distal portion of applicators with knot leaders, knot rods, and foot held on short applicator at cross section plane b by foot loop.

FIG. 6C is a frontal view along short applicator looking from cross section a to b showing foot, foot loop, and sutures coming from needle nose housings.

FIG. 6D is a frontal view looking proximally along long applicator from cross section a.

FIG. 6E is a plan view of short applicator including knot rods, knot leaders, wire snares, and snare holders with sutures (dots) in suture slots at cross section a.

FIG. 6F shows sutures moved in suture slots to cross sectional plane b where sutures push wire snares out of suture slots and into snare holders.

FIG. 6G shows sutures moved in suture slots to cross sectional plane c where sutures are no longer pushing wire snares out of suture slots so snares return into suture slots behind sutures.

FIG. 6H shows wire snares at cross section d where knot leaders surround sutures after operator pulls knot leader slightly to take it out of snare holder.

FIG. 6I is a side view of long and short applicators with spring roller holding them and a foot held by foot loop on long applicator at cross sectional plane f.

FIG. 6J is a frontal view looking from cross section a to f with foot loop holding foot with sutures coming from needle nose housings then turning toward viewer.

FIG. 6K shows sutures (as dots) in suture slots looking from a to f.

FIG. 6L is a plan view of long applicator distal to spring roller plus leader board.

FIG. 6M shows an alternative configuration of a shallow groove in the side of suture slot at cross section j.

FIG. 6N shows a plan view of crossing knot leaders from short applicator and long applicator combined in the pattern of a slip knot around knot rods.

FIG. 6O is a plan view of knot leaders in a slip knot not showing cross over.

FIG. 6P is a plan view of knot rod holder as the operator sees it.

FIG. 7A is a plan view of detail near and distal to tightener gate at cross section f.

FIG. 7B is a frontal view of details near tightener gate at f.

FIG. 7C is a side view of details near and distal to tightener gate at f.

FIG. 7D is a side view of the long side of wire snares in two suture slots being pulled by attached knot leader through snare tightener as short side enters snare tightener.

FIG. 7E shows unbent and bent short sides of snare wire in snare tightener.

FIG. 7F shows small scale snare wire with ends in snare tightener.

FIG. 7G is a side view of details of resistance film adhering to tightener gate and snare tightener.

FIG. 7H is a frontal view of details of resistance film adhering to tightener gate and snare tightener.

FIG. 7I is a plan view of overlaid short and long applicators with slip knot of knot leaders around knot rods and wire snares that hold sutures ready to be pulled by leader boards.

FIG. 8A is a side view of short applicator and long applicator after sutures have been pulled through knot rods and knot rod holder has removed knot rods.

FIG. 8B is a plan view of short and long applicators overlaid showing slip knots made with sutures and sutures extending distally through suture slots.

FIG. 8C shows sutures pulled from between short and long applicators by operator but still attached to leader boards and looped through vessel wall.

FIG. 8D shows a side view of pinch sleeve with slot stoppers between h and k as shown on short and long applicators in FIG. 8G.

FIG. 8E is a frontal view of pinch sleeve, slot stoppers and overlaps at section h.

FIG. 8F is a frontal view of pinch sleeve, slot stoppers and overlaps at section k.

FIG. 8G shows the effect of pinch sleeve forcing together short applicator and long applicator distal to spring roller and slip knot at cross section I where applicator ends have moved knot to vessel wall.

FIG. 8H is a frontal view of two sutures in long applicator suture slots and slot stoppers from pinch sleeve in short applicator suture slots at cross section h.

FIG. 8I shows frontal view of rail sutures coming toward viewer with loop sutures wrapped around them in slip knot distal to applicator ends at cross section I.

FIG. 8J shows frontal view of two sutures in long applicator suture slots at cross section h with cutter end about to cut sutures as described in FIGS. 9A-G.

FIG. 9A is plan view of portion of cutter channel that turns around snare holder to cross adjacent suture slot at right angle to cutter channel leading to push knob.

FIG. 9B is a detail plan view of cutter channel turning to cross adjacent suture slot at a right angle with cutter pusher pushed by push knob and cutter end ready to cross.

FIG. 9C is a plan view after operator pushes push knob to most distal position, thus pushing cutter end across suture slot.

FIG. 9D shows three side views of push knob pushing cutter pusher and cutter end moving in cutter channel around the right turn at cross section "h" thus disappearing from side view.

FIG. 9E shows three frontal views of cutter end at cross section h as it moves across suture slots to cut the two sutures.

FIG. 9F is side view of push knob and distal ends of short and long applicators after applicator ends have pushed slip knot to vessel and cutter end is about to cut sutures in suture slot at cross section h.

FIG. 9G is a frontal view of applicator ends at cross section h after cutter end has cut sutures in suture slots.

FIG. 9H is side view of push knob and distal ends of short and long applicators just after cutter end moves across suture slots and cut sutures in suture slots at cross section h.

FIG. 9I shows suture loops tied in vessel wall with knot which has been severed by cutter end thus freeing device for removal from body.

DETAILED DESCRIPTION OF THE PREFERRED EMBODIMENTS

Having thus described the figures, methods and means in accordance with the present invention are now described with reference thereto. It should be understood that steps described for each process may be omitted or the order changed or performed simultaneously without deviating from the spirit or scope of the invention. It should be understood that a specific application situation involving a vessel, such as an artery may have somewhat different characteristics than another application with another vessel, whether artery, vein or other tubular structure of the body such as urethra or even skin and each application situation may require somewhat different dimensions, numbers in a plurality, angle of entry, or other invention characteristics. Since the first applications are expected to be closing an opening in the common femoral artery, dimensions, numbers and terms used in the specification are consistent with an ideal sutured closing for that case without intent to limit dimensions, numbers, angles or terms to that case.

The following description of preferred embodiments should be read with reference to the drawings, in which the elements in different drawings are numbered in like fashion. The drawings, which are not necessarily to scale nor of exact shape, nor of actual angle of entry which in application varies with individual cases, thus depict or represent specific embodiments and are not intended to limit the scope of the invention. Distances between suturing elements are provided as examples based on ideal manual suturing practices with the body open so all distances given should be considered approximate and illustrative. Examples of materials, construction, dimensions and manufacturing processes are provided for various elements but merely as a representation of current manufacturing practice which may change during the patent period. Also, it is contemplated that any optional feature of the inventive variations described may be set forth and claimed independently, or in combination with any one or more of the features described herein. Reference to a singular item includes the possibility that there is a plurality of the same items present but not seen in the view being described. More specifically, as used herein and in the appended claims, the singular forms "a," "an," "said," and "the" include plural referents unless specifically stated otherwise. In many cases there is more than one of an element having a singular name and associated number key thus plural usage of a singular element is used to refer to "them" rather than "it" thus the articles allow for "at least one" of the subject item in the description above as well as the claims below. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in the claims shall allow for the inclusion of any additional element irrespective of whether a given number of elements are enumerated in the claim, or the addition of a feature could be regarded as transforming the nature of an element set forth in the claims. Except as specifically defined herein, all technical and scientific terms used herein are to be given as broad a commonly understood meaning as possible while maintaining claim validity. Although the foregoing invention has been described in detail for purposes of clarity of understanding, it will be obvious that certain modifications may be practiced within the scope of the appended claims. Those skilled in the art will recognize that many of the examples provided here have suitable alternatives which may be used now and in the future.

FIG. 1A is a schematic representation of angles of entry for percutaneous devices between skin and vessel wall 28. An intravascular device must generally follow the angle used by other devices for their prior entry though a deviation of 30 degrees or more from the original is possible—depending primarily on obesity of patient. The angle of entry of other devices from skin to vessel may be at any angle but 40-60 degrees is common.

FIG. 1B shows a generalized image of the present device as it would appear for use in angles of entry of 40, 60 and 90 degrees. It is evident that it is impractical to represent an intravascular suturing device in this specification for every possible angle and that each alternative is an obvious variation for other entry angles. Therefore the convention is applied to all figures in this specification that the angle of entry is 90 degrees. Though this angle of 90 degrees is not the most commonly used at the present it is easy to convert such an image to any entry angle that will be needed in practice. Practical considerations do not interfere with the conventions used in specifications to represent shapes, angles and sizes without specifying exact numbers.

FIG. 1C is a plan view at cross section c and a frontal view of the cross section between front face and back face of centerboard 1 (cross sectional views are used so components interior to the faces need not be shown as dashed lines). Centerboard 1 has a length greater than width and width greater than thickness, the length having a distal end and a proximal end, the width terminating in edges, and the thickness being between front and back faces. Centerboard 1 has a longitudinal axis running in the proximal-distal direction equally distant from edges and faces. The ends and edges of centerboard 1 are straight and faces are flat except for protuberances and a semi-circular shaped suture cove 16 on distal end shaped to conform to the shape of vessel wall 28 and having a slot in thickness open to distal end from edge to edge suitable for storing suture loops. In an alternative configuration suture cove 16 is made of a soft elastic material such as polybutadiene to avoid injury to vessel wall 28 and may have greater thickness than hard material in centerboard also to avoid injury to vessel wall 28 opposite vessel opening to be closed. Centerboard 1 is made of high tensile strength metal, carbon fiber, or polymer, shaped and connected by processes appropriate for the material which may include injection molding, bending, cutting, drilling and bonding to form various openings, channels and attached components. The proximal end is located outside the body where an operator can manipulate it and the semi-circular distal end is located inside free edge slit across 30. The length of centerboard 1 must accommodate the size of the patient being treated but nominally be about 15-25 cm. Thickness of centerboard 1 is about 1 mm and width is pre-selected to be about one half the circumference of the free edge of the opening in vessel wall 28 that is to be closed. Thus when centerboard 1 is advanced into the vessel opening, the pre-selected width causes the free edge of the circumference of the opening to be stretched thereby closing it together into a relatively straight slit pressing against the front and back faces of centerboard 1. This shape is called free edge slit across 30 when view is looking along the longitudinal axis of vessel wall 28 and free edge slit side 29 when vessel wall 28 is viewed from the side. Openings in arteries or other vessels to be closed are not so large that this relatively straight line of free edge is as long as half the vessel circumference, so the vessel wall 28 opposite the opening retains some or all of its natural curvature. The semi-circular shape of suture cove 16 is to conform to this shape. One cue that the centerboard is in the vessel is the resistance of the semi-circular suture cove 16 of centerboard 1 pushing against vessel wall 28 on the side opposite the opening. Visual cues are discussed with contrast fluid below. Guidewire channel 17 is located along the longitudinal axis of centerboard 1, having a proximal end and distal end with lumen therebetween and being of smaller diameter than thickness of centerboard 1 and having a proximal port 39 at proximal end extending through the back face, and distal port 46 extending through front face near distal end but proximal to suture cove 16. A guidewire 48, not part of the device, is normally located in the artery and extends through the skin at the angle it was entered into the body. The operator is careful not to remove the guidewire while threading the guidewire through distal port 46, guidewire channel 17, and proximal port 39, then, with guidewire 48 already being within vessel wall 28 the operator advances centerboard 1 on guidewire 48 through opening in vessel wall 28 so distal end of centerboard 1 is inside vessel wall 28. A sheath, also not part of this device, but normally in the opening around guidewire 48 is removed before centerboard 1 is advanced on guidewire 48 because opening cannot be converted to a slit with the circular sheath in the opening. A fluid channel 38 is included in two alternative configurations, one configuration for introducing contrast fluid inside vessel wall 28, the other for inflating two balloons 24 on either side of centerboard 1, which may be inflated with contrast fluid. Both alternative configurations provide visual images for use in determining when centerboard 1 is positioned properly within vessel wall 28. In both alternative configurations fluid channel 38 is located adjacent to guidewire channel 17 and has fluid port proximal 68 adjacent to proximal port 39. In the alternative configuration for introducing contrast fluid inside vessel wall 28 the fluid port distal 77 for fluid channel 38 is located adjacent distal port 46. In the alternative configuration for inflating two balloons 24, (shown in more detail in FIG. 1J) fluid channel 38 is divided immediately distal to the plurality of needle openings 40 into two sections of fluid channel 38 that turn at a right angle and run toward opposite edges of centerboard 1 where each section of fluid channel 38 has a has a fluid port edge 78. In the alternative configuration for placing contrast fluid within vessel wall 28, fluid port edge 78 is open to do this. In the alternative configuration where inflation fluid is introduced for inflating two balloons 24, fluid port edge 78 opens into balloons 24 attached to each of the two edges of centerboard 1 thus making the width of centerboard 1 more adjustable than the manufactured pre-selected width alone and providing the option of having contrast fluid in balloons 24 for visualization. Of course centerboard 1 is also dense enough to be fluoroscopically or ultrasonically visualized for purposes of properly positioning it within vessel wall 28. Threaded post 3 is a cylinder of about 1-2 mm diameter made of the same material of and being attached to or molded with centerboard 1 and extending proximally about 5-7 mm from the proximal end in line with the longitudinal axis and having male threads located around the cylinder that self-align with female threads 32 in a screw turner 25 as shown in FIG. 2B. In an alternative configuration there is a stopper 43, a small protrusion of generally semi-circular shape of about 1-2 mm radius located on each edge near the distal end of centerboard 1 and when centerboard 1 is properly placed between outboard legs 47 of outboard 19 the small protrusions of stopper 43 will stop distal movement of centerboard 1 within outboard 19 by engaging keeper 42 on outboard 19. Suture cove 16 is located distal to needle openings 40 and continues distally to the distal end of centerboard 1 and having a slot somewhat less in thickness than the thickness of, and extending from side to side of centerboard 1 provides a cove for storing suture loops 15. There is a plurality (six is the number used for illustration in this specification) of needle openings 40 about 2 mm apart along a straight or slightly bowed imaginary line across the width of centerboard 1 each needle opening 40 being an open cavity having a proximal end a distal end with length between about 1.5 and 4.5 and parallel to the longitudinal axis of centerboard 1, with width about 0.5 mm, and thickness equal to the thickness of centerboard 1 with distal ends immediately proximal to suture cove. There is a plurality of separator wire channels 5 having a distal end and proximal end with lumen therebetween being of round or oval cross section about 0.5 mm in diameter, running parallel to the longitudinal axis in line with and open to needle openings 40 on distal ends and cross slots 34 on proximal ends. Cross slots 34 have proximal ends and distal ends and are of the same shape, size and number as needle openings 40. A plurality of separator wires 4 are of slidably smaller diameter than separator wire channels 5, each having a distal and proximal end with high tensile strength metal wire therebetween and initially located in cross slots 34 and separator wire channels 5, and not in needle openings 40 but with each distal end of each separator wire 4 having a wedge end 41 initially located at proximal end of needle openings 40. In each needle opening 40 there is a needle pair 44, one of a plurality of needle pairs having two needles and each needle having a needle nose 10 temporarily connected to a needle shaft 11 by a frictional dowel 12. Needle nose 10 is about 1 mm in length and tapering from about 0.5 mm diameter on distal end to a sharp point on proximal end and having a nose indent 45 located on the taper or, in an alternative configuration, between needle nose 10 and needle shaft 11. Needle shaft 11 is about 0.5 mm in diameter, length from about 1 to 4 mm and with distal end of each needle shaft 11 being attached to distal end of needle opening 40 in which each needle pair is located thus causing needle noses to point toward wedge ends of separator wires 4 in separator wire channels 5. The slightly curved shape of free edge slit across 30 is intended to represent the actual situation in a vessel. After suturing is completed this line will be curved as was the original curvature of the vessel, however before suturing the line will be relatively straight due to stretching. The exact shape will probably vary among individuals, so the slightly curved line used in drawing is an example, not intended to be an exact shape. Needle openings 40 are about 2 mm apart along a generally straight but somewhat curved line between edges, the generally straight line having the curvature of the free edge slit across 30 of actual vessels.

FIG. 1D is a cross section side view of centerboard 1 with the distal end of centerboard 1 shown entering free edge slit side 29. It is seen in this side view that cross slot 34 extends from front face to back face of centerboard 1 as do needle openings 40 and separator wire 4 is located in cross wire slot 34 and in separator wire channel 5 when in its most proximal position. In that most proximal position separator wire 4 is not in needle opening 40 but wedge end 41 is aligned between needle shafts 11 and needle noses 10 of needle pair Suture cove 16 has a slot between centerboard faces starting on a line between edges where the distal ends of needle openings 40 are arrayed and continuing distally to the distal end of centerboard 1. A plurality of suture loops 15 are stored in suture cove 16 and suture ends 14 of each suture loop 15 are swaged or otherwise attached to a needle nose 10 or friction dowel 12 permanently attached to needle nose 10 of each needle pair 44. Operator has removed a sheath (not part of this device) from needle opening 40 in vessel wall 28 and placed guidewire 48 (also not part of this device but normally located inside vessel wall 28) in to and out of centerboard 1, entering through distal port 46, through guidewire channel 17 and leaving through proximal port 39. Then operator advances centerboard 1 on guidewire 28 through opening to be closed in vessel wall 28.

FIG. 1E is a cross section front and plan view at cross section b of frame 13 which is in the shape of a six-sided box with top and bottom removed, being made of the same material as centerboard 1, having inside dimensions slidably greater than the cross section of centerboard 1 and thus capable of sliding on the cross section of centerboard 1, and with sides about 3-4 mm in length parallel to the longitudinal axis of centerboard 1, thickness of sides adjacent faces of centerboard 1 being about 1-2 mm and thickness of sides adjacent edges of centerboard 1 being sufficient for an operator's fingers to grip and move frame 13 from position at proximal end to distal end of cross slots 34 a distance of about 2-5 mm on the length of centerboard 1. The proximal end of centerboard 1 is not shown in the plan view of this figure so dotted lines are not required to show the plurality of cross wires 33 attached across frame 13 that are located within cross slots 34 with each being attached at the center, at a right angle to the proximal end of one of the plurality of separator wires 4.

FIG. 1F has a side view showing the situation before operator moves frame 13 distally on centerboard 1.

FIG. 1G has a side view showing the situation after operator moves frame 13 distally on centerboard 1 the length of cross slot 34 thus moving cross wire 33 through cross slot 34 and moving separator wires 4 the same distance. Movement may be in the distal or proximal direction.

FIG. 1H is a side view after frame 13 has been pushed to the distal position and shows the effects of that movement within free edge slit side 29. Cross wire 33 on frame 13 has moved distally in cross slot 34 and pushed separator wire 4 distally in separator wire channel 5 which causes wedge end 41 to move the same distance in needle opening 40 thus forcing needle pair apart at the pre-selected angle of wedge end 41 which places needle noses 10 of each needle pair about 2 mm apart with 1 mm on each side of free edge slit side 29. Each needle nose 10 has a nose indent 45 and an attached suture end 14.

FIG. 1I is a frontal view of centerboard 1 with frame 13 pushed to the distal position. This figure shows the alternative configuration for introducing contrast fluid into fluid port proximal 68, through and fluid channel 38 into artery through fluid port distal 77.

FIG. 1J is a plan view of needle openings 40 with needle shafts 11 and needle noses 10 in the unbent positions and with the alternate configuration of balloons 24 in uninflated state at cross section a.

FIG. 1K is a plan view of needle pairs in the unbent position and balloons 24 inflated at cross section a.

FIG. 1L is a frontal view at cross section a of needle pairs 44 and inflated balloons 24 within vessel wall 28. Since the length of the slit generally is not as long as half the circumference of the artery, the balloons 24 do not escape through the slit but take positions in "pockets" they form on either side of the vessel wall, thus tending to keep the distal end of centerboard 1 in artery 28.

FIG. 1M is a plan view that shows suture loops 15 in suture cove 16 where cove walls 18 are placed to form suture compartments 36 for suture loops 15 of each needle pair 44. Suture loops 15 are in suture compartments 36 with cove walls 18 between suture compartments 36, all within suture cove 16.

FIG. 1N shows a plan view of needle pairs spread apart.

FIG. 1O is a detail side view of needle pair showing two needle shafts 11 with friction dowel 12 holding needle noses 10 to needle shafts 11, and suture ends 14 of suture loop 15 swaged to or otherwise attached to needle nose 10 of each needle pair or to friction dowel 12 permanently attached to needle nose 10. The suture loop 15 for this pair of needle noses 10 is seen in suture cove 16 which has an open distal end that allows suture ends 14 of suture loop 15 to be pulled out of suture cove 16 by movement of needle nose 10 but the suture loop 15 remains inside the artery while suture ends 14, attached to needle noses 10 in needle nose housings 21 are removed in each foot 20 of outboard 19 as they and centerboard 1 are removed from patient's body. Suture loops may be made of any material sutures are normally made of, may be non-biodegradable or biodegradable, and may be any standard size used to close openings in vessel being sutured. Separator wire 4 is seen in separator wire channel 5 about to enter needle opening 40 before operator moves frame 13 in the distal direction on centerboard 1.

FIG. 1P shows the situation after operator has moved frame 13 in the distal direction causing separator wire 4 to enter needle opening 40 and push wedge end 41 between needle shafts 11. Needle opening 40, being equal in thickness to centerboard 1 allows needle shaft 11 and needle nose 10 to be bent outside center board 1 on opposite sides of the approximately linear free edge of free edge slit side 29. Wedge end 43 has an angle preselected to bend needle shafts 11 apart so as to place needle noses 10 of a needle pair 44 about 1 mm from each side of free edge side slit 29. Nose indent 45 is shown between needle nose 10 and needle shaft 11 in this alternative configuration.

FIG. 1Q shows in cross section two shapes that separator wires 4 may take and how the cross section of wedge end 41 has a curved shape to fit the cylindrical shape of needle shaft 11.

FIG. 2A is a side view of outboard 19 which has a proximal end, a distal end and therebetween two outboard legs 47 and a contiguous blockhead 49 which joins outboard legs 47. Outboard 19 is made of high tensile strength metal, carbon fiber, or polymer, shaped and connected by processes appropriate for the material which may include injection molding, bending, cutting, drilling and bonding to form various openings, channels and attached components. Each outboard leg 47 has a length greater than width and width greater than thickness, the length having a distal end and a proximal end, the width terminating in edges, and the thickness being between front and back faces. The length of each outboard 19 must accommodate the size of the patient being treated but nominally be about 15-30 cm. Thickness of each outboard leg 47 is about 1 mm and width about 1 mm greater than width of centerboard 1 on each edge of each outboard leg 47. In an alternative configuration that portion of the edge that is about 1 mm greater than width of centerboard on each edge turns at a right angle and extends half way across the gap between outboard legs 47 from where blockhead 49 joins outboard legs 47 to about 10 mm proximal to the location of keeper 42 thus confining centerboard 1 within outboard legs 47 except near the distal end where stopper 43 moves in the distal-proximal direction for about 4-5 mm when centerboard 1 is moved between outboard legs 47. The turned edge also adds to rigidity of outboard 19, which may be further increased by joining touching edges with a temporary adhesive. This alternative configuration is shown in FIG. 2A and in 2B, where it more easily seen in plan view, while the preferred configuration is shown in other figures. Foot 20 protrudes outward about 1-2 mm from the face of, and on the distal end of each outboard leg 47 and also extends about 1-2 mm outside each edge of outboard leg 47 and extends approximately 1-2 mm from distal end of outboard 19 in the proximal direction. Each foot 20 contains a plurality of needle nose housings 21, each being at a location that places it in line with one needle nose 10 when needle pair 44 is separated by wedge 41 thus placing each needle nose about 1 mm from each side of free edge slit across 30. In the extension of foot 20 outside the edges of outboard 47 there is a protrusion of about 0.5 mm, called keeper 42, protruding in the direction opposite that which foot 20 protrudes from face of outboard leg 47 thus filling the gap between outboard legs 47 that lies outside the edges of outboard legs 47. Keeper 42 is thus positioned to prevent centerboard 1 from moving outside the edge of outboard legs 47 on the distal end and provide a means for stopper 43 on the edge of centerboard 1 to prevent keeper 42 from moving past it in the distal direction. Thus when outboard 19 is properly placed with respect to centerboard 1, stopper 43 of centerboard 1 is immediately proximal to keeper 42 thus locating each needle nose housings 21 in each foot 20 is outside (adventitial to) free edge slit side 29 and about 1-2 mm from deployed needle noses 10 on the inside of free edge slit side 29 with vessel wall 28 between. Outboard legs 47 are joined by blockhead 49. Blockhead 49 is of irregular shape in exterior and interior dimension but is generally described as follows using the shapes shown in figures to assist in the description. Blockhead 49 extends from the proximal end of outboard 19 about 15 mm to outboard legs 47 with thickness about 5-6 mm and width being about 2-3 mm greater than the width of centerboard 1 for about 5 mm from proximal end then equal to width of centerboard 1 for another 8-10 mm to point where blockhead joins outboard legs so outboard legs 47 have a distance between that is slidably greater than thickness of centerboard 1. This equal width for 8-10 mm provides an area for operator to grip the protrusions on frame 13. The inside dimensions of blockhead 49 from the proximal end to the joining with outboard legs 47 are; (1) unthreaded hole 51 in the shape of an empty cylinder of circumference slidably greater than that of threaded post 3 and with centerline on the longitudinal axis of centerboard 1 extending about 4-5 mm in the distal direction from proximal end of outboard 19 to initial location of proximal end of centerboard 1, (2) centerboard slot 72, that has a thickness and width slidably greater than those of the proximal end of centerboard 1 and extending from proximal end of outboard 1 to for about 7-9 mm where frame 13 is initially located, (3) frame slot 73, slidably greater in cross section than cross section of frame 13 and extending within blockhead 49 from centerboard slot 72 about 3-4 mm a distance about equal to the distance frame moves which is the length of cross slot 33 and needle opening 40. This is the distance required to move wedge ends 41 of separator wires 4 from proximal ends to distal ends of needle openings 40 thus spreading needle noses across free edge side slit 29. Blockhead 49 joins outboard legs 47 immediately distal to frame slot 73 and being wider than outboard legs 47 in the section from proximal end of outboard 19 to frame slot 73 constitutes a barrier to the movement of centerboard 1 located in centerboard slot 72 to any point outside the edges of outboard legs 47.

FIG. 2B shows a cross sectional view of screw turner 25 and a front view of outboard 19 and plan views at cross sections a, b, and e. showing the alternative configuration of turned edges of outboard legs 47 that prevent centerboard 1 from moving outside the edges of outboard legs 47. Blockhead 49 has a width about 1-2 mm wider than centerboard 1 on each edge from proximal end of outboard 19 through centerboard slot 72 and is of the same width as centerboard 1 through the section having frame slot 73 which is slidably greater than the thickness of frame 13 which moves within frame slot 73. Blockhead 49 is the same shape in the preferred and alternative configuration of edges of outboard leg 47. Foot 20 is shown to contain tapered needle nose housings 21. The shape of needle nose housings 21 is that of an empty cylinder closed in foot 20 toward the proximal end of outboard legs 47 and open at the opposite end and being tapered to be larger near the open distal end thus providing a larger target for entry of needle nose 10 positioned opposite the open end. Access slot 23 in outboard leg 47 is shown to be in position to align with proximal port 39 thus allowing guidewire 48 (with fluid channel with that alternative configuration) to emerge from centerboard 1. Shown in dashed lines within blockhead 49 are unthreaded hole 51, which allows passage of threaded post 3 into female threads 32 of screw turner 25, centerboard slot 72, and frame slot 73. Outboard legs 47 are shown with protrusions in this alternative configuration not shown in subsequent figures.

FIG. 2C is a plan view of foot 20 looking in the distal direction which shows the proximal end of needle nose housings 21 to be closed by foot 20 and shows protrusions, each called keeper 42 outside the two edges of outboard legs 47. Keeper 42 keeps edges of centerboard 1 from moving outside the edges of outboard legs 47 and also prevents stoppers 43 on the edges of centerboard 1 from moving distal to keeper 42, thus forcing needle nose housings 21, located outside vessel wall 28 to be at a distance from needle noses 10, located inside vessel wall 28, that is slightly greater than the thickness of vessel wall 28.

FIG. 2D is a plan view of foot 20 looking in the proximal direction. The open ends of the taper of needle nose housings 21 are seen as well as keepers 42. The taper on nose housings 21 is represented by two concentric circles to indicate a flare constituting a larger target for each aligned needle nose 10 to enter.

FIG. 2E is a plan view of screw turner 25 at cross section "g" and side view through a cross section of screw turner 25 and the proximal section of outboard 19 where split blockhead 50 holds outboard legs 47 apart to slidably contain centerboard 1 and frame 13. This is an alternative configuration in which split blockhead 50 is of the same material and replaces blockhead 49. Split blockhead 50 is divided in two halves along the plane midway between outboard legs 47, with each outboard leg 47 attached to one half of split blockhead 50 and having outside dimensions such as allow a flexible detachable surround 22 that is in the shape of 4 sides of a box with top and bottom removed to slidably fit around the proximal end of split blockhead 50 to hold the halves together. A tongue and groove 71 is located around surround 22 and split blockhead 50 to prevent surround 22 from accidentally being removed. Thus the alternative configurations of separated and un-separated outboard legs 47 are essentially equivalent except when surround 22 is not around the proximal end split blockhead 50, and outboard legs 47 may be moved slightly outward to engage spurs 31 on each foot 20, and each outboard leg 47 may be removed from the body independently of the other which may reduce the volume of what is removed at one time. Also shown is a front and plan view of screw turner 25 of generally cylindrical shape with female threads 32 on the centerline. Screw turner 25 may be made of the same material as centerboard 1. The female threads 32 fit the male threads of threaded post 3 and threads are held in contact for a short distance and are self-aligned before rotation starts. Rotation causes threaded post 3 to continue through female threads 32. Alternative configurations are obvious, including those that increase mechanical advantage with different thread pitch.

FIG. 2F is a cross section view at f of surround 22 around split blockhead 50 with unthreaded hole 51 and centerboard slot 72.

FIG. 2G shows outboard legs 47 slightly rotated outward from the faces of centerboard 1 which places the distal side of foot 20 slightly farther away from the free edge of free edge slit side 29. One or more spurs 31, in the shape of wire-like protrusions of a stiff material that will adhere to the distal side of each foot 20 being about 0.1-0.3 mm in length and diameter and protruding at an acute angle with sides of acute angle opening toward faces of outboard legs 47 and being in planes that are at a right angle with respect to distal side of foot 20 will engage free edge slit side 29 and draw and hold free edges closer against centerboard 1 by a tweezers-like action.

FIG. 2H is a side view of the distal portion of suturing placement component 2 in free edge slit side 29 with centerboard 1 between the outboard legs 47 of outboard 19 showing frame 13 has not been moved to separate needle shafts 11 of needle pair 44 that are inside free edge slit side 29, but that needle nose housings 21 are positioned outside free edge slit side 29 to be aligned with needle noses 10 when needle shafts 11 are separated a pre-selected distance on the longitudinal axis by keeper 42 and stopper 43. Suture loop 15 is shown in suture compartment 36 with suture ends 14 swaged or otherwise attached to needle noses 10 of needle pair 44.

FIG. 2I is a cross section at d of plan view of frame 13 with attached cross wires 33 located in cross wire slots 34 between split blockhead 50.

FIG. 3A is a detail view of needle nose housing 21 and needle nose 10 held to needle shaft 11 by friction dowel 12. Friction dowel 12 is permanently attached to needle shaft 11 and frictionally to needle nose 10. Needle nose 10 has nose indent 45 in the nose in this figure, and not in the alternative configuration being between needle nose 10 and needle shaft 11 as was shown in FIG. 1G. Housing detent 27 is shown as one or more protrusions in needle nose housing 21 which are normally of the smaller diameter of indent 45 but are pushed back by the tapered point of needle nose 10 until the smaller diameter of nose indent 45 allows them to return to their normal constricted diameter which then prevents needle nose 10 from being removed from needle nose housing 21. Therefore, when needle shaft 11 is pushed in the proximal direction by reversing the direction of turning screw turner 25, needle shafts 11 are separated from needle noses 10 which remain in nose housings 21 with suture ends 14 while needle shafts 11 remain inside free edge slit side 29.

FIG. 3B shows an alternative configuration of the housing detent 27 and nose indent 45 in which friction dowel 12 is permanently attached to needle nose 10 and frictionally to needle shaft 11. In this arrangement nose indent 45 may be placed between needle nose 10 and needle shaft 11 but in this figure nose indent 45 is in the same location it was in FIG. 3B. Spring clip 26 is placed in needle nose housing 21 as the housing detent 27 that expands as needle nose 10 is pushed in needle nose housing 21 and then closes into nose indent 45 to capture needle nose 10. This spring clip 26 is ancient technology as are many means of trapping an object by a detent moving into an indent after the indent has moved through the detent like an arrow only to be prevented from backing up.

FIG. 3C shows alternative configurations of needle pairs with friction dowel 12 permanently attached to needle nose 10 and frictionally attached in needle shaft 11 or vice versa and nose indent 45 located in needle nose 10 and located between needle nose 10 and needle shaft 11, all being functionally equivalent ancient technologies.

FIG. 3D is an alternative configuration in which there is a plurality of blunt ends 35, one on the end of each separator wire 4 (rather than a wedge end 41) and blunt end 35 being connected to the center of bridge wire 37 which is initially in the shape of a loop made of a resilient material such as spring steel located between and attached to needle shafts 11 of each needle pair 44. Bridge wire 37 is not easily seen between needle shafts 11 of needle pair 44, so its shape is shown to the left and below the number 37.

FIG. 3E shows bridge wire 37 is of a length that when pushed straight by blunt end 35 of each separator wire 4 pushes needle shafts 11 a distance that places needle noses 10 of each needle pair about 1 mm away from each face of centerboard 1. This is shown in the figure where blunt end 35 is shown after being moved distally thus pushing bridge wire 37 to its straight length which causes needle shafts 11 to move apart the pre-selected distance equal to the length of separation bridge wire 37.

FIG. 4A is a cross section side view of centerboard 1 and outboard 19 as they are introduced into the body and through free edge slit side 29 in vessel wall 28 by operator. Screw turner 25 is also shown slightly screwed into threaded post 3. FIG. 4B is a front view of centerboard 1 and outboard 19 as they are introduced into the body by operator is advancing them on guidewire 48 threaded through centerboard 1 from distal port 46 to proximal port 39 exiting outboard 19 at access slot 23. (The length is not to scale and erased sections are used to show this). An assistant applies pressure to the artery to maintain hemostasis while the physician performs the steps described in FIG. 1C to remove the sheath from the opening in vessel wall 28 and thread guidewire 48, that is already in the artery, through the centerboard and out access slot 23 in outboard then advance centerboard 1 and outboard 19 on guidewire 48 until distal end of centerboard 1 is inside vessel wall 28 where it is seen in free edge slit across 30. The entry of centerboard 1, with width pre-selected to force the vessel opening to close to a slit, and with each foot 20 outside vessel wall 28 on either side of the slit may be felt by operator to be in correct position but in addition other cues are available. Stopper 43 is touching keeper 42 which causes needle noses 10 to be the correct distance from each needle nose housing 21 in each foot 20, thus placing each foot 20 on the adventitial side of vessel wall 28 and apart from needle noses 10 by about the thickness of vessel wall 28. Keeper 42 also prevents centerboard 1 from moving outside outboard 19. Frame 13 is shown in the proximal position with separator wire 4 in separator wire channel 5 just proximal to needle opening 40 so needle pair has not been pushed apart. Also threaded post 3 is self-aligned in female threads 32 of screw turner 25 but screw turner 25 has not been turned to cause threaded post 3 to move centerboard 1 in the proximal direction within female threads 32. The alternative configuration with balloons 24 is not shown in this figure, but if the alternative configuration with balloons 24 (as shown in FIG. 4D) is being used they are inflated now to (in effect) extend the width of centerboard 1 by stretching free edge slit across 30 tighter.

FIG. 4C is a side view of suture placement component 2, namely centerboard 1 in outboard 19, after frame 13 has been pushed to the distal position. This causes cross wires 33 attached across frame 13 to move in cross slots 34 in the distal direction and separator wires 4 attached to the center of cross wire 33 are moved the distance distally which is the same as the length of needle opening 40 thus causing wedge 41 of separator wire 4 to enter needle opening 40 and separate needle pair 44 by a pre-selected distance so needle noses 10 become aligned with needle nose housings 21 outside (adventitial to) free edge slit side 29. Suture ends 14 are attached to needle noses 10 and suture loops 15 between suture ends 14 are stored in suture compartments 36 for each needle pair 44.

FIG. 4D is a front view of centerboard 1 and outboard 19 after frame 13 has been pushed to distal position. Cross wires 33 move distally in cross slots 34 causing attached separator wires 4 to move distally in separator wire channels 5 moving wedge end between needle pairs 44 in needle openings 40.

FIG. 4E is a side view after screw turner 25 has been turned a sufficient number of turns to cause threaded post 3 to enter female threads 32 thus drawing together centerboard 1 and outboard 19, and forcing needle noses 10 through vessel wall 28 and into needle housings 21 with the substantial force of the threads of an inclined plane needed to penetrate vessel walls 28 when they are calcified. Frame 13 moves with the movement of centerboard 1 to the proximal position it was originally in while wedge end 41 remains between needle pairs This movement of centerboard 1 forces each needle nose 10 of each needle pair through vessel wall 28 where they are located about 1 mm from the free edge of free edge slit side 29. The needle nose housings 21 are outside (adventitial to) free edge slit side 29 immediately opposite each needle nose 10 so push with the same force against each needle nose 10. Having the mechanical advantage of a screw and the flanged opening of needle nose housings 21 positioned opposite and pushing with equal force creates a situation more conducive for a needle to pierce a calcified artery than a surgeon can create without the device. For arteries that are not calcified the procedure and device are the same though it is obvious that threads of greater pitch will move screw turner 25 the same distance with fewer turns and less mechanical advantage. The side view shows needle noses 10 in needle housings 21. Suture ends 14 attached to each needle nose are trapped with the needle noses 10 to which they are attached when housing detents 27 lodge in nose indents 45.

FIG. 4F is a front view of what is described in FIG. 4E.

FIG. 4G is a side view of suture placement component 2, with centerboard 1 moved in the distal direction within outboard 19 by operator turning screw turner 25 in the opposite direction while also holding frame 13 in the proximal position. This causes needle shafts 11 attached to moving centerboard 1 to disengage from needle noses 10 being held in needle nose housings 21 by breaking temporary friction connection of friction dowel 12. Also needle shafts 11 return to the position inside centerboard 1 as operator is holding frame 13 in proximal position thus preventing separator wires 4 with wedge ends 41 from moving distally with needle shafts 11. This view shows the alternative configuration with balloons 24 and fluid channel 38 which would be deflated at this time when those two alternative configurations are used. Centerboard 1 and outboard 19 are now ready for the operator to remove from the body and the physician releases pressure on vessel opening to determine if pressure of pulsing blood is reduced by free edge slit side 29 being held against centerboard 1 by suture loops 15 pulling on free edge of vessel opening. If so, centerboard 1 outboard 19 are removed from the body by physician pulling them out singly or together depending on the alternative configurations of split blockhead 50 or blockhead 49, but in either case needle noses 10 are drawn out of the patient's body in nose housings 21 with suture ends 14 attached to each needle nose 10 of each needle pair 45 while suture loop 15 remains in the artery or other vessel. This device provides alternative configurations; suture tying component 103, and suture clip component 104, for simultaneously joining all suture ends 14 at free edge with either knots or clips.

FIG. 4H is a cross sectional front view of centerboard 1 and outboard 19 as described with FIG. 4G. This view shows the alternative configuration with balloons 24 and fluid channel 38 which would be deflated at this time when those two alternative configurations are used.

FIG. 5A shows suture clip component 104 with a view of the situation after centerboard 1 and outboard 19 of intravascular placement device 2 are removed from the body and free edge slit side 29 is held together by a length of suture loop 15 with suture ends 14 attached to needle noses 10 in needle nose housings 21 in each foot 20 of outboard legs 47. The preferred configuration with blockhead 49 is shown but the alternate configuration with split blockhead 50 presents essentially the same situation. Cross clamp 52 is shown opened to place cross bars 53 extending from arms of cross clamp 52 on each side of sutures loops 15. Cross clamp 52 and cross bars 53 are made of a high tension metal such as stainless steel. Cross clamp 52 is generally shaped like scissors that cross on an axle and have open handle loops for insertion of thumb on one arm and one or more fingers in the handle on the other arm and on the end opposite the handles on each arm is a cross bar 53 extending at a right angle from the plane of closing of the handles for a distance slightly greater than the width of the plurality of suture loops 15.

FIG. 5B is a frontal view of the situation shown in FIG. 5A with a cross sectional view of cross bar 53 at a-a and an alternative configuration of tension adjustor 59 for adjusting the length of each suture loop 15 so the straight line of sutures originally produced may be adjusted to form a curved line more consistent with the natural curvature of the artery and also to more conveniently hold suture loops 15 without having to hold the two outboard legs 47 and attached foot 20 with needle nose housings 21 and attached suture loops 15. Extending at a right angle to the plane of closure of cross clamp 52 are two curved cross bars 53, (one obscuring the other in this view). The curvature of cross bars 53 is preselected to be congruent with the natural curvature of the cross section of vessel wall 28. In an alternative configuration there are two suture shields 58, each in the shape of a planchet in two unequal halves separated by a curved line of separation, attached at a right angle to and on the ends of cross bars 53, one half on each end of cross bars 53 furthest from cross clamp 52 and one half of each of the other suture shield 58 on ends of cross bars 53 closest to cross clamp 52, thus the larger unequal half extends beyond the plane in which the plurality of suture loops 15 lie, constituting a barrier to the movement of any suture loop 15 outside suture shield 58, thus ensuring suture loops 15 will not slip outside the ends of cross bars 53. Suture shields 58 are shown in side view of FIG. 5D. Strip holder 55 is a recessed groove in facing sides of each cross bar 53 having straight rectangular sides and curved to run parallel to the curvature of cross bars 53 from one end of cross bar 53 to the other. One strip holder 55 holds female strip 56 and the other strip holder 55 holds male strip 57. Female strips 56 and male strips 57 are curved strips of metal or polymer material that may safely remain in the body, such as non-magnetic stainless steel or titanium or a biodegradable or non-biodegradable polymer. In cross section, as shown in a-a, each is shaped on one side to fit in strip holder 55 and shaped on the other side so male strip 57 has the general shape of an arrow head that congruently fits in the shape of female strip 56 so the arrowhead cannot be removed once in. The surfaces of the arrowhead shape are almost touching and have a plurality of turns (e.g. three turns for the simple arrowhead shape) to prevent suture loops 15 trapped in the cross section from moving toward vessel wall 28 and keep male strip 57 and female strip 56 permanently joined after cross clamp 52 is opened for removal from the body. The joined male strip 57 and female strip 56 must be released from strip holders 55 after cross clamp 52 is opened and removed from the body. There are alternative configurations for release of male strip 57 and female strip 56 from strip holders 55, the simplest, and thus preferred, being making the width of strip holder 55 slidably greater than male strip 57 and likewise with female strip 56 to hold them in place until after they are pushed into each other trapping suture loops 15 between them—at which point strip holders 55 should release the joined male strip 57 and female strip 56.

Since strip holders 55 may fail to release one or both joined female strips 56 and male strips 57 when cross clamp 52 is opened for removal from the body, three alternative configurations are provided to ensure the release, one being shown in the cross section view a-a in this figure. Scissors cutter 54 is located slightly closer to the handles of cross clamp 52 than are strip holders 55 and are in the shape of two rectangular strips extending at right angles from cross bar 53 so placed as to slide past each other to cut suture loops 15 between them with an amount of applied pressure that is greater than that required to propel male strip 57 into female strip 56. Thus only after suture loops 15 are trapped and sealed between male strip 57 and female strip 56 are the ends of suture loops 15 cut. Break away strips 74 are used in the alternative configuration shown in this figure and compression breakers 76 in another alternative configuration. The third alternative is a mechanical means of release shown in FIG. 5H. Break away strips 74 and compression breakers 76 are made of a crystalline material that disintegrates into small grains when a pressure equal to its tensile strength is applied. This material must be one that can safely remain in the body, Salt is absorbable by the body and has a wide range of tensile strengths created as a function the temperature at which it is processed by melting and cooling. Sugar is an alternative crystalline material that is slightly more adhesive (sticky) but not as safe as salt for absorption by all patients. The pressure applied to force male strip 57 into female strip 56 may be used to cause the crystalline material of compression breaker 76 to break away and form grains or the additional pressure applied to force scissors cutters 54 to cut suture loops 15 after female strip 56 and male strip 57 are joined may be used to break the temporary crystalline bond of breakaway strips 74. The alternative configuration using holder slots 75 and breakaway strips 74 is shown in cross section a-a in this figure and the other alternative configurations are shown in FIG. 5C and FIG. 5H. Holder slots 75 are slots made at a right angle to and within the straight rectangular sides of strip holder 55 and in male strip 57 and female strip 56 at locations to align them with holder slots 75 in strip holders 55 as shown in a-a. Break away strips 74 are of the same curvature as and slidably smaller than strip holders 55 in which they are located, thereby holding male strip 57 and female strip 56 in strip holders 55. The alignment causes male strip 57 and female strip 56 to extend into strip holders 55 only so far that they do not completely fill the furthest extent of the closed end of strip holders 55. Therefore, when cross bars 53 are squeezed the additional amount required to bring scissors cutters 54 past each other to cut suture loops 15, female strip 56 and male strip 57 are pushed to the end of strip holders 55, breaking break away strips 74 as shown in FIG. 5F. Before higher pressure is applied for joining male and female strips 56, the operator uses only slight pressure between male strip 57 and female strip 56, sufficient to keep suture loops 15 untangled while cross bar 53 is being pushed along suture loops 15 toward free edge slit across 30. Greater pressure is only applied after reaching vessel wall 28 to force male strip 57 into female strip 56 with sutures between, and still more pressure to cause the two blades of scissors cutter 54 to pass each other and cut suture loops 15 free of their length outside the body after suture loops 15 are trapped between the male strip 57 and female strip 56. The same additional pressure will break the alternative configuration of breakaway strips 74 in holder slots 75 which releases male strips 57 and female strips 56 from strip holders 55 so cross clamp 52 may be removed from the body with the assurance that it is not stuck to either male strip 57 or female strip 56 which remain in the body holding suture loops 15 together.

FIG. 5C shows the preferred configuration at cross section a for holding retaining male strip 57 and female strips 56 in strip holders 55 by friction only, and thus simpler and preferred. There are alternative configurations for release of male strip 57 and female strip 56 from strip holders 55, the simplest, and thus preferred, being making the width of strip holder 55 slidably greater than male strip 57 and likewise with female strip 56 to hold them in place until after they are pushed into each other trapping suture loops 15 between them—at which point strip holders 55 should release the joined male strip 57 and female strip 56. Since strip holders 55 may fail to release one or both joined female strips 56 and male strips 57 when cross clamp 52 is opened for removal from the body, three alternative configurations are provided to ensure the release.

FIG. 5D shows an alternative configuration in which compression breakers 76 are located between and touching strip holders 55 and the sides of male strips 57 and female strips 56 and thus provide the friction that holds female strip 56 and male strip 57 in their strip holders 55. Compression breakers 76 may be applied while in the liquid state or after being cooled in molds and slid between strip holders 55 and male strips 57 and female strips 56.

FIG. 5E shows the alternative configuration of two suture shields 58 in the shape of a planchet divided in two unequal halves by a curved line of separation being in the shape an arc with chord not centered on mid line between unequal halves and the separation being of sufficient width to allow cross clamp 52 to force male strip 57 into female strip 56 and for further closing to bring the two halves of scissors cutter 54 together to cut suture loops 15. Holder slots 75 are shown in one suture shield 58 to allow loading of breakaway strips 74 during manufacture and assembly when that alternative configuration is used with the alternative configuration of suture shields 58.

FIG. 5F is a view from the end of cross bar 53. The predetermined curvature of cross bar 53 extending from a perigee at each end to the apogee at center applies also to male strip 57, female strip 56, strip holder 55, break away strip 74 holder slot 75 and compression breaker 76. The shapes of each have a cross section at each point along their extent but when viewed from the side the cross sections cannot be seen but only a continuous stack of cross sections going from perigee to apogee as shown in FIGS. 5F and 5G. The same stacking view applies to scissors cutter 54, but it is not applied in FIGS. 5F and 5G as the purpose of these figures is to show how the added force that causes scissors cutter 54 to close and cut suture loops 15 also forces the joined male strip 57 and female strip 56 to be pushed farther into strip holder 55 thus breaking break away strip 74 into grains that do not inhibit the separation of strip holder 55 and male strip 57 and female strip 56 which are joined before the grains are produced by exceeding the tensile breaking strength of the material. Break away strips 74 are of the same curvature as and slidably smaller than strip holders 55 in which they are located, thereby holding male strip 57 and female strip 56 in strip holders 55. The alignment causes male strip 57 and female strip 56 to extend into strip holders 55 only so far that they do not completely fill the furthest extent of the closed end of strip holders 55. Therefore, when cross bars 53 are squeezed the additional amount required to bring scissors cutters 54 past each other to cut suture loops 15, female strip 56 and male strip 57 are pushed to the end of strip holders 55, breaking break away strips 74 as shown in FIG. 5G.

FIG. 5G is a view of the alternative configuration in which compression breakers 76, are located between male strip 57 and its strip holder 55 and between male strip 57 and its strip holder 55 to show how pressure forces male strip 57 and female strip 56 further into strip holders 55 either after or before they are joined thus matching the tensile strength of compression breakers 76 which can be pre-selected to be that of either the pressure required to cause male strip 57 to be forced into female strip 56 or the pressure required to cause scissors cutter 54 to cut suture loops 15 after male strip 57 has been forced into female strip 56. Either amount of pressure can be used to cause compression breakers 76 to disintegrate into grains that do not inhibit the separation of strip holder 55 and male strip 57 and female strip 56.

FIG. 5H is a view showing the effect of additional pressure that forces male strip 57 and female strip 56 further into strip holders 55 causing break away strip 74 to disintegrate into grains that do not inhibit the separation of strip holder 55 and male strip 57 and female strip 56 which were joined before the grains are produced by exceeding the tensile breaking strength of the material.

FIG. 5I shows an alternative configuration for ensuring the separation of strip holder 55 and female strip 56 and male strip 57 by mechanical means. A cross section of strip holder 55 and a fragment that represents both female strip 56 and male strip 57 is shown after sufficient pressure has been applied to join them. The sides of strip holder 55 are not rectangular with respect to the closed end but are tilted to become narrower toward the closed end. The shape of the sides of male strip 57 and female strip 56 adjacent the sides of strip holders 55 are tilted to conform to the adjacent sides of strip holders 55. At a plurality of locations along the length of female strip 56 and male strip 57 are slant channels 62, open cylinders extending from one side to the other of male strip 57 and female strip 56 where slant channels 62 open toward each side of strip holder 55. Two slant end rods 60 located in each slant channel 62 are slidably smaller and of the same cross section as slant channel 62 and movable only with the amount of force required to close scissors cutter 54. One end of each slant end rod 60 extends into the space between strip holders 55 and the sides of female strip 56 and male strip 57 adjacent to and touching the sides of strip holders 55. Thus the friction for holding female strip 56 and male strip 57 in strip holders 55 is between these ends of slant end rods 60 and the sides of strip holders 55. The other end of each slant end rod 60 is truncated to slant in the opposite direction from the other slant end rod 60 and is located congruently adjacent to release rod 61 which is truncated at two angles to be congruent with the ends of slant end rods 60 located contiguously with the truncation at two angles of release rod 61. Release rod 61 is located in release channel 63 which is a cylinder that intersects with the center point of slant channel 62 and continues to the end of male strip 57 and female strip 56 facing the closed end of strip holder 55. Since the end of release rod 61 is slanted to match the slants of each slant end rod 60 and the other end of release rod 61 is touching the closed end of strip holder 55, the additional pressure required to close scissors cutter 54 is applied to the ends of slant end rods 60 providing the friction for holding female strip 56 and male strip 57 in strip holders 55 thus when female strip 56 and male strip 57 are moved by toward the closed end of strip holder 55 with sufficient force to move slant rods 77 in slant channel 62 the truncated end of release rod 61 is pushed against the closed end of strip holder 55 thus pushing female strip 56 and male strip 57 out of strip holder 55 as there is no longer any friction exerted between the ends of slant end rods 60 against the sides of strip holder 55.

FIG. 5J is an example of an alternative configuration (to sharp turns) to prevent suture loops 15 from moving in the direction of vessel wall 28. In this alternative configuration a plurality of barbs 70, that are wire-like protrusions about 0.1-0.3 mm in length and diameter located in the cross section of separation between male strip 57 and female strip 56 where suture loops 15 are forced by male strip 57 entering female strip 56. Barbs 70 are attached at an acute angle to a portion of the surfaces of female strip 56 and male strip 57 and sides of acute angle open in the direction opposite that of movement of suture loops 15 toward vessel wall 28. Thus barbs 70 are attached to a portion of the surface of male strip 57 on one side of the separation and to a portion of the surface of female strip 56 on the other side of the separation as shown. Also, the direction of travel of male strip 57 into female strip 56 is not inhibited by barbs 70 since the acute angle of their attachment opens in the direction that is opposite to that of travel. Thus barbs 70 on female strip 56 and male strip 57 open from the acute angle of attachment in opposite directions with both being against the movement of suture loops 15 toward vessel wall 28 as shown.

FIG. 5K is an example of an alternative configuration to prevent male strip 57 from separating from female strip 56 by attaching a plurality of loops and hooks 9 made of material such as polyester or nylon about 0.1-0.3 mm in length and diameter located in the cross section of separation between male strip 57 and female strip 56 at touching surfaces of male strips 57 and female strips 56. The plurality of loops and hooks 9 are not to scale.

FIG. 5L is a view from free edge slit across 30 as operator uses handles to push cross clamp 52 and cross bar 53 toward vessel wall 28 while holding suture loops 15 in sufficient tension to keep them untangled while also keeping free edge slit side 29 closed as can be determined by no blood spurting from the vessel opening plus the operator's sense of feel for the correct tension. When the physician feels the end come against the artery he/she takes the action of squeezing handles of cross clamp 52 thus forcing male strip 57 into female strip 56 and thus trapping one side of sutures 15 between the small cross section of space between. This also cinches suture loop 15 tighter by the length of the small cross section of space suture loop 15 is pushed into, thus pulling tissue of free edge slit across 30 to create a slightly greater mass of tissue between adjacent sutures which tends to create lateral pressure on adjacent sutures which in turn causes the natural curvature of vessel wall 28 to return, thus avoiding constriction of artery lumen. Physicians will learn how much the sutures shorten when drawn through the pathway between male strip 57 and female strip 56 and this will vary with the alternative configuration pre-selected for the application.

FIG. 5M is a cross section view of an example of a shape joined female strips 56 and male strips 57 may take when their shapes have a plurality of sharp turns that suture loops 15 caught by the turns must take between male strip 57 and female strip 56 after joining. The suture loops 15 are located in the cross section between the almost touching surfaces of joined male strip 57 and female strip 56 but are not shown as doing so would add nothing but subtract from the clarity of the figure.

FIG. 5N shows the cross section has a plurality of sufficiently sharp turns to hold suture loops 15 without cutting but preventing suture loops 15 from moving in the cross section separation in the direction of the vessel opening.

FIG. 5O is a view of cross clamp 52 attached to middle of cross bar 53, an alternative configuration that may be advantageous over attachment on end of cross clamp 52 in certain body shapes or certain size openings in vessel wall 28.

FIG. 5P is a plan view of tension adjustor 59 in the shape of a six-sided box cut in two halves across the sides parallel to the ends of the box with the two halves held together on one side by hinge 65 and on the opposite side by clasp 66 and clasp button 67 that may be closed on each other when the box is placed in the closed position. The area within the box is recessed with respect to box sides and this recessed area 69 is where friction pads 64 are located in each half of tension adjustor 59. The friction is pre-selected to be sufficient to prevent suture loops 15 from slipping through friction pads 64. The length of tension adjustor 59 is pre-selected to be somewhat greater than the width of the plurality of suture loops 15, the width less than the length and the thickness less than the width. The thickness may be on the order of 1-2 mm. The length of tension adjuster 59 is placed across the plurality of suture loops 15 and then closed and locked by placing clasp button 67 in clasp 66. Friction pads press against each other with suture loops 15 between when tension adjustor 59 is closed on suture loops 15. The fit and friction of friction pads is such that tension adjustor 59 holds suture loops 15 unless operator pulls on a specific pair of suture loops 15, which causes that pair to move. Suture loops 15 may be cut free of their attachment to needle noses 10 when the alternative configuration of tension adjustor 59 is used.

FIG. 5Q is a side view of an open tension adjustor 59.

FIG. 5R is an end view of a closed tension adjustor 59.

FIG. 6A is a side view of short applicator 88 and long applicator 82, each having a distal end and a proximal end with rectangular boards therebetween constructed of a hard, relatively inflexible, high tensile strength material such as metal or polymer and each having a longitudinal axis and being in the general shape of the two halves of a spring clothes pin, but long half being several times length of short half. The length of short applicator 88 being about 2-4 cm and long applicator 82 pre-selected for patient size, but generally about 15-25 cm, width being less than length and pre-selected to be about as wide as 2 mm×(1+number of sutures in plurality of sutures) which is also about the width of free edge of opening in vessel to be closed to a slit called free edge slit side 29. Thickness of short applicator 88 and long applicator 82 is generally less than width and increasing from about 1-2 mm at distal end, called applicator nose 93, to about 2-4 mm on proximal ends. A plurality of knot rod channels 94, being empty cylinders located proximal to suture slots 97 (suture slots 97 are not seen in side view but in plan view of FIG. 6C) are at a right angle to longitudinal axis of and running through the thicknesses of short applicator 88 and concentrically running through about half the thickness long applicator 82. Knot rod channels 94 are arranged in columns and rows each about 2 mm apart, with columns generally in line with suture slots 97. In this example there are 9 knot rod channels 94 in column seen in side view as dotted lines, and there are adjacent columns not seen in a side view but seen in plan view of FIG. 6C. A plurality of snare holders 92 are located between a plurality of suture slots 97 that are not clearly visible in side view but are indicated by a dotted line that extends toward applicator nose 93 at distal end of short applicator 88 and long applicator 82. They are discussed when clearly visible in plan view of FIG. 6C. Cutter 89, cutter pusher 90, and push knob 91 provide the means of cutting suture ends 14 after suture loops 15 have been tied in knots. They are shown here and discussed in association with FIGS. 9A-E.

FIG. 6B is a side view of short applicator 88 and long applicator 82. Knot rods 87 are initially located in knot rod channels 94. Diameter of knot rod channels 94 is slidably larger than knot rods 87 in short applicator 88 and sufficiently less in diameter in long applicator 82 to cause enough friction with knot rods 87 to prevent them from being easily removed once pushed in. Knot rod holder 83 is gripped by operator to slide knot rods 87 in and out of knot rod channels 94 simultaneously as one end of each knot rod 87 is attached to knot rod holder 83 which is a solid block of metal or polymer about 1 cm thick, and of sufficient length and width to hold all knot rods 87 that are arrayed in rows and columns as are knot rod channels 94, each about 2 mm apart. Foot loop 81 loops around foot 20 and is an aid to transferring sutures from foot 20 to short applicator 88 by holding foot 20 as it is moved along the increasingly thick short applicator 88 to cross section planes a, b, c, d, e, and shown at b in this figure. Foot loop 81 is of a circumference sufficient to wrap around foot 20 and either short applicator 88 or long applicator 82 in cross section as shown, and made of an elastic material, such as polyisoprene or polybutadiene which may be attached to an inflexible material, such as stainless steel where the inflexible, portion is located between, and the flexible portion outside short applicator 88 and/or long applicator 82. Foot 20 is seen in side and front views and is one of two which were removed from patient's body at end of procedure with suture placement component 2 and each contains a plurality of suture loops 15 attached to a plurality of needle noses 10 trapped in a plurality of needle nose housings 21.

FIG. 6C is a frontal view of a generalized image looking from a to b along short applicator 88 that shows applicator nose 93 at distal ends of short applicator 88 and shows foot 20 and foot loop 81 as it appears [on short applicator 88] from applicator nose 93. Suture slots 97 are seen and they are about 2 mm apart along width. Sutures 15 extend from needle noses 10 in needle nose housings 21 in foot 20 through suture slots 97 then turn at a right angle to run toward applicator nose 93, (shown as a dot representing suture cross section.)

FIG. 6D is a view along long applicator 82 from a to b. Wire snares 84 are seen as lines across suture slots 97 but not discussed here.

FIG. 6E is a plan view of the distal portion of short applicator 88 and an extension of knot leaders 79 to rail leader board 96 where they are attached. A plurality of suture slots 97 extending from distal ends of short applicator 88 and long applicator 82 (long applicator not shown in this figure) about 3-8 mm toward proximal ends and being parallel to longitudinal axes each have a width of about 0.2-0.7 mm and thickness equal to thickness of short applicator 88 and long applicator 82 where suture slots 97 are located. The plurality of sutures 15 from foot 20 are pushed within suture slots 97 as foot 20 is moved along short applicator 88 here seen at cross section plane a. In the preferred configuration which does not include spring roller 86, this is accomplished by operator holding short applicator 88 and long applicator 82 in his/her hands without aids. The dots labeled 15 in suture slots 97 represent sutures 15 in suture slots 97 as seen along the suture's own longitudinal axis. A plurality of wire snares 84 are positioned in snare holders 92 as the means of snaring sutures 15 as they are pushed proximally in suture slots 97 by movement of foot 20 and foot loop 81. Snare holders 92 are depressions in the facing surfaces of short applicator 88 and long applicator 82, located between suture slots 97 and distal to an alternative configuration named tightener gate 99 that is simply the proximal end of suture slots 97 with alternative configurations of snare tighteners 85. The shape of a snare holder 92 is like that of a strung and bent simple "D" bow from handle located at tightener gate 99 to bow end near applicator nose 93 where the bow string is attached and bent back sharply as with a drawn bow string. A plurality of wire snares 84, each having the same shape as and initially located in each snare holder 92, have a proximal end located in snare holder 92 at tightener gate 99 and a distal end in snare holders 92 near applicator nose 93. The side of wire snare 84 that is in the shape of a bent bow is longer than the short section in the shape of bow string. The short side extends into adjacent suture slot 97. The long, bow shaped side of wire snare 84 is swaged or otherwise attached to the distal end of a knot leader 79. The depression that is snare holder 92 in short applicator 88 is the same shape as the corresponding depression of snare holder 92 in long applicator 82 which have open faces facing each other. The short (bow string) side of wire snare 84 enters and crosses adjacent suture slot 97 at a point proximal to cross section plane a and this point is shown to be at cross section plane b in FIG. 6D. Each knot leader 79 has one end attached to the long side of a wire snare 84, and extends proximally to bend around a plurality of knot rods 87 in a particular pattern that is one side of slip knot 80 then continue proximally to attached to rail leader board 96 which is a solid object of metal or polymer of planchet shape located proximal to short applicator 88. In this specification a particular slip knot is used as example and it requires 9 knot rods 87. Other slip knots may be used and such variants have names such as Roeder, Meltzer, Tayside, Tenn. slider, etc. Each has a different pattern that may require a different numbers of knot rods 87 to bend around, but all have one relatively straight side and the other side is wrapped around it. This straight side is sometimes called "rail" and sometimes "post". The other side is often called the "loop strand". The terms "rail" and "loop" will be used here and the slip knot will have the generic name. The rail side of knot leader 79 is attached to wire snares 84 in short applicator 88 and attached to rail leader board 96 in this example but this could be reversed in another example. The loop sides of sutures 15 (shown in FIG. 6H) are snared by wire snares 84 in long applicator 82, extend through the same knot rods 87 around which rail sutures are bent, and are attached to loop leader board 98.

FIG. 6F shows sutures 15 moved in suture slots 97 in the proximal direction to the plane of cross section b. At cross section plane b, sutures 15 push wire snares 84 out of suture slots 97 and into snare holders 92.

FIG. 6G shows sutures 15 moved in suture slots 97 in the proximal direction to cross section plane c. At cross section plane c, sutures 15 are no longer pushing wire snares 84 out of suture slots 97 so wire snares 84 spring back to their previous positions in suture slots 97 but now sutures 15 are trapped by snare wires 84.

FIG. 6H shows wire snares 84 surrounding sutures 15 after knot leaders 79 with distal ends attached to wire snares 84 have been pulled a short distance by operator pulling rail leader board 96 attached to the proximal end of those knot leaders 79 thus drawing knot leader 79 and wire snares 84 in the proximal direction. Each suture 15 from short applicator 88 is snared by a wire snare 84 and moved proximally as shown and discussed in more detail in FIGS. 7A-D.

FIG. 6I is a side view of short applicator 88 and long applicator 82 with an alternative configuration that may provide greater assurance that they will be held together than does the friction of knot rods 87 in knot rod channels 94 of long applicator 82 thus making it easier for operator to handle. This alternative configuration provides a spring roller 86 located near the proximal end of short applicator 88 in shaped depressions in short applicator 88 and long applicator 82 corresponding to size of roll, thus constituting a rotational axis between short applicator 88 and long applicator 82, with wire in roll made of a springy metal, such as spring steel with diameter about 0.5-1 mm and roll having a plurality of turns of about 3 mm diameter. Number of turns may be equal to the plurality of suture loops 15 in foot 20. The wire ends of spring roller 86 are curved to wrap around, and bend back toward each other, outside short applicator 88 and long applicator 82 to hold them together as does the spring in a spring clothes pin. There may be shaped depressions outside short applicator 88 and/or long applicator 82 for the ends of spring roller 86 to fit in. This side view also shows the other foot 20 placed on long applicator 82 with foot loop 81 holding foot 20 as operator has pushed it proximally from cross section planes a to e and finally to cross section plane f which is the proximal end of suture slot 97 and location of an alternative configuration called tightener gate 99. In the side view, the pattern of knot leaders 79 is shown as a series of loops around knot rods 87. The knot leaders from long applicator 82 continue proximally, as do those from short applicator 88, (through loops of spring roller 86 when that alternative configuration is used) to be attached to loop leader board 98 a planchet of non-slippery material of a size that can be grasped between thumb and forefinger to pull attached knot leaders 79 simultaneously.

Thus knot leaders in short applicator 88 are in the pattern of the rail side of slip knot 80 and attached to rail leader board 96 and knot leaders 79 in long applicator 82 are in pattern of loop side and attached to loop leader board 98 (or vice versa). The front view [is a generalized image looking from a to f that] shows sutures 15 in short applicator 88 already placed in suture slots 97, snared by wire snares 84 and cut free of the foot 20.

FIG. 6J is a frontal view of a generalized image looking from cross section a to f along long applicator 82 that shows applicator nose 93, foot 20 held on long applicator 82 by foot loop 81 and sutures 15 extending from needle nose housings 21 in foot 20 and entering suture slots 97, which] are about 2 mm apart along width. Sutures 15 then turn at a right angle to run toward applicator nose 93, (shown as a dot representing suture cross section.).

FIG. 6K is a frontal view of short applicator 82 from a to f. Sutures 15 are seen as dots in suture slots 97. A wire snare 84 has snared each suture 15 but this cannot be seen in this view but snare details are shown in FIGS. 7A-H.]

FIG. 6L is a plan view of long applicator 82 distal to spring roller 86. Short applicator 88 and long applicator 82 have the same shape of wire snares 84 and snare holders 92 so the snaring situations for long applicator 82 are the same as for short applicator 88 from planes a-e, and thus are not repeated except the pattern of knot leader 79 around knot rods 87 is different for this loop side than for rail side in short applicator 88, and knot leaders 79 are attached to loop leader board 98 in long applicator 82 and to leader board 96 in short applicator 88.

FIG. 6M shows a short snare groove 6 that is an alternative configuration that may be provided in the side of suture slots 97 [along cross section j] for the end of the short side of wire snare 84 to move in and thus ensure that it does not catch on the rail or loop side of suture loop 15 as it passes to snare it.

FIG. 6N shows rail and loop knot leaders 79 from short applicator 88 and long applicator 82 combined in the pattern of slip knot 80 around knot rods 87. The image shows which knot leader 79 crosses over which other knot leader 79, where the knot leader 79 underneath is shown as erased and the knot leader 79 on top as continuous.

FIG. 6O is a small image that is used in other figures. It does not show the detail of which goes under and over but represents the over and under configuration shown in FIG. 6N. Other patterns of slip knot 80 may be used and they may require a different number of knot rods 87.

FIG. 6P is a plan view of knot rod holder 83, previously specified but not shown in plan view. The operator sees this view as he/she grips knot rod holder 83 to place knot rods 87, which are attached to the opposite side of knot rod holder 83.

FIG. 7A is a detail plan view of the area around alternative configuration tightener gate 99 and the area distal to tightener gate 99. Short applicator 88 and long applicator 82 each have snare holders 92, wire snares 84, snare detent 100, and the distal end of suture slots 97 which is tightener gate 99 when used in an alternative configuration. The components of the alternative configuration are snare tighteners 85, short snare groove 6, and resistance film 95 and all have the same structure and appearance in short applicator 88 and long applicator 82. FIG. 7A is used to represent both. The plurality of gates in tightener gate 99 are the proximal ends of suture slots 97 closed by resistance film 95 attached to the surface of tightener gate 99. Resistance film 95 is a thin film made of a high tensile strength material such as paraylene-polyxylylene or polyester polyethrlene-teraphtalate (PET) and coated with an adhesive. The adhesive causes resistance film 95 to adhere to the surface of tightener gate 99 and to a plurality of snare tighteners 85. Each snare tightener 85 has the shape of an oval ring and is made of a material that will retain its shape and be harder than the material of wire snare 84, such as stainless steel. Each snare tightener 85 is held by adhesion to resistance film 95 at the location of the proximal end of suture slots 97 which is a gate in tightener gate 99 when covered by resistance film 95 which is cut within the oval ring of each snare tightener 85 to allow the two arms of wire snare 84 to pass through unimpeded. Each knot leader 79 attached to long arm of wire snare 84 is initially located within the oval ring of snare tightener 85 and the short arm of wire snare 84 enters the oval ring when the long arm is pulled proximally by pulling knot leader 79 [as shown in FIG. 7D). Short snare groove 6, shown in FIG. 6M allows short arm of wire snare 84 to pass around the side of suture loop 15 in suture slot 97 without becoming entangled. The two arms of each wire snare 84 fit tightly in the oval ring of snare tightener 85 and tighten on the side of suture loop 15 that is snared by wire snare 84 as the two arms are pulled within snare tightener 85. Resistance film 95, resists being torn apart or breaking adhesion and so holds snare tightener 85 in place as substantial force is exerted to force the arms of wire snare 84 together in the oval ring of snare tightener 85 but finally tears and/lor loses adhesion, thus opening gates to passage of the rail or loop side of suture loop 15 in that gate. Wire snare 84 is made of a material such as titanium or a gold alloy that is sufficiently malleable to bend around knot rods 87 and sufficiently springy to be held under compressive tension in snare holder 92 and to spring behind that side of suture loop 15 to snare it after wire snare 84 was pushed aside. A plurality of wire snares 84, each shaped like a bow with bowstring bent back from bow end, are initially located in a plurality of snare holder 92 and the bowstring portion of each is the short side initially extending from the bend back between bow and bow string into suture slot 97 as shown. The bow or long side of each wire snare 84 is held between snare detent 100 and distal end of snare holder 92 under slight compressive tension which holds it in snare holder 92. The end of wire snare 84 that is detained by snare detent 100 is attached by swaging or other means to the distal end of one of a plurality of knot leaders 79. Each knot leader 79 has a distal end and a proximal end with flexible material therebetween. The material may be any of those normally used for sutures including metal, cotton, silk, gut, and polymer.

FIG. 7B shows a detail frontal view of two suture slots near cross section f in which the long side of wire snare 84 is being pulled by attached knot leader 79 through snare tightener 85 while the short side of wire snare 84 has not yet started to enter snare tightener 85.

FIG. 7C is a side view of a suture 15 in a suture slot 97 at cross section a before being snared by wire snare 84 as suture 15 is moved to cross section f. Snare detent 100 may be seen near cross section f holding wire snare 84 in snare holder 92 before operator pulls on knot leader 79 which will pull attached wire snare 84 around detent 100 and through snare tightener 85 toward knot rod 87, shown as a fragment in this view.

FIG. 7D shows a detail plan view in two suture slots 97 near cross section f of the long side of wire snare 84 being pulled by attached knot leader 79 through snare tightener 85 which adheres to resistance film 95 while the short side of wire snare 84 starts to enter snare tightener 85 while tightening around the side of suture loop 15 in each snare FIG. 7E shows two images in a detail view of both arms of wire snare 84 within snare tightener 85 making wire snare 84 tight around the side of suture 15 in that snare tightener. Comparing the two images shows that the short end on wire snare 84 may be intentionally or unintentionally bent back around snare tightener 85 and this does not impair the tightness of fit of wire snare 85 around suture 15. The short end may be bent back as wire snare 84 is pulled around knot rods 87 or when there is no snare tightener 85 as in the preferred alternative configuration.

FIG. 7F A small image is shown to aid in recognition of wire snare 84 in figures that do not show the detail FIG. 7E does.

FIG. 7G is a side detail view of resistance film 95 adhering to tightener gate 99 and to snare tightener 85. One side of suture loop 15 has been snared by wire snare 84 and snare tightener 85 is pulling the short and long sides of wire snare 84 tightly around that side of suture loop 15. Sufficient pulling force has not yet been exerted on wire snare 84 to force resistance film 95 to tear and/or lose adhesion, so this is the final tightening of wire snare 84 before resistance film 95 is torn which then offers no more resistance in open gates of tightener gate 99 to suture loops 15. At this point suture connections to foot 20 are severed by knife of scissors by operator, making suture loops 15 attached only to wire snares 84.

FIG. 7H is a frontal view of what is shown in and discussed regarding FIG. 7G.

FIG. 7I is a plan view intended to represent both short applicator 88 and long applicator 82. The portion[s] of short applicator 88 and long applicator 82 distal to tightener gate 99 are the same and directly in line with each other so one image represents both. The portion proximal to tightener gate 99 is common to short applicator 88 and long applicator 82 and shows wire snares 84 from short applicator 88 have been pulled out of their snare holders 92 and pulled through tightener gate 99 of short applicator 88 where they are located while wire snares 84 in long applicator 82 are being pulled out of their snare holders 92 and are passing through their tightener gate 99. They will be pulled into the common area where knot leaders 79 from short applicator 88 have already been drawn and then both rail leader board 96, and loop leader board 98 will be pulled drawing knot leaders with sutures snared in wire snares 84 from both short applicator 88 and long applicator 82 through the slip knot pattern around knot rods 87. As this is done the pattern knot leaders have is transferred to suture loops 15. Thus suture loops 15 when they have gone through knot rods 87 have the slip knot pattern that knot leaders 79 had. The rail leader board 96 and loop leader board 98 are pulled by operator pulls to draw each set of knot leaders 79 and snared sutures 15 into slip knots 80 made of suture loops 15.

FIG. 8A is a side view of short applicator 88 and long applicator 82 after suture loops 15 have been drawn through knot rods 87 to form slip knot 80. These are the rail and loop sides of suture loop 15 which is still located across free edge slit across 30 in vessel wall 28 as rail and loop sides extend proximally through rail leaders 79 to rail leader board 96 and loop leader board 98. Operator has removed the knot rods 87. Alternative configuration of spring roller 86 is shown at cross sectional plane g for holding short applicator 88 and long applicator 82 together like the spring roller on a spring clothes pin. Cutter channel 102, cutter 89 and push knob 91 are shown but not described with this figure.

FIG. 8B is a plan view showing that shown in side view FIG. 8A without cutter components being shown. Slip knots 80 are made with sutures 15 and sutures 15 extend distally through suture slots 97 and proximally between loops of spring roller 86, then, being interrupted by the symbol for discontinuity, continuing where sutures 15 are still snared by wire snares 84 attached to knot leaders 79 connected to rail leader board 96 and loop leader board 98. These attachments are not all shown in the discontinuity.

FIG. 8C shows sutures 15 attached to knot leaders 79 by wire snares 84 and knot leaders 79 attached to rail leader boards 96 and loop leader board 98. Operator has taken sutures 15 between his/her fingers and pulled them out from between short applicator 88 and long applicator 82 and slightly tightened the loop sides of slip knots 80 so loop side will slip on the rail side. This places slip knot 80 in position to be slipped down to artery side slit 29 after the distal ends short applicator 88 and long applicator 82 are pinched together on their distal ends by pinch sleeve 101. Operator has removed knot rods 87 so distal ends of short applicator 88 and long applicator 82 can be pinched together on distal ends.

FIG. 8D shows pinch sleeve 101 which operator places around distal end of short applicator 88 and long applicator 82 to pinch them together. Pinch sleeve 101 is made of a relatively inflexible, tough, thin membrane of polymer shaped to fit around the slanting shape of short applicator 88 and long applicator 82 where suture slots 97 are located and to hold short applicator 88 and long applicator 82 together at that location by means of adhesive sides that are attached to surface where pinch sleeve 101 is applied. Another object of pinch sleeve 101 is to place slot stoppers 8 in suture slots 97 thus restricting rail and loop sides of suture loops 15 to a location in long applicator 82 in line with cutter ends 89. Slot stoppers 8 are slidably less wide than suture slots 97 and attached to pinch sleeve 101 in such a manner that they are aligned with suture slots 97. The shape of slot stoppers 8 is triangular in depth and the same length as suture slots 97 in which they are located. The triangular shaped suture stoppers increase in depth from cross sectional plane h to plane k. The triangular shapes of slot stoppers 8 entering suture slots 97 in short applicator 88 completely fill those suture slots 97 so sutures 15 cannot be located in slots 97 of short applicator 88. The triangular shape and size of slot stoppers 8 entering suture slots 97 in long applicator 82 are such as to leave only space for rail and loop sides of suture loops 15 that are directly in line with cutter ends 89 as described with FIGS. 9A-E.

FIG. 8E shows a frontal view of pinch sleeve 101 at cross section h. The adhesive membrane has one or two overlaps 7 of adhesive surface to fasten applicators together.

FIG. 8F shows a frontal view of pinch sleeve 101 at cross section k. Slot stoppers 8 fill suture slots of short applicator 88 completely and partially fill suture slots of long applicator 82.

FIG. 8G shows the effect of pinch sleeve 101 forcing the distal portion of short applicator 88 and long applicator 82 together. Rail and loop sides of suture loops 15 are forced into long applicator 82 by slot stoppers 8. Slip knots 80, being larger than, and outside suture slots 97 are pushed by applicator nose 93 of closed short applicator 88 and long applicator 82 to free edge slit side 29 and as slip knot 80 advances the "rail" sutures 15 are pulled in the distal direction by rail leader board 96 until slip knot 80 is pressing against open slit 29 in vessel wall 28. Pulling rail leader board 96 and loop leader board 98 at the same time makes slip knot 80 a permanent knot and ready to be cut loose from suture tying component 103.

FIG. 8H shows a frontal view at cross sectional plane h where pinch sleeve 101 is around long applicator 88 and short applicator 82 with slot stoppers 8 filling suture slots 97 in short applicator 88 completely and partially filling suture slots 97 in long applicator 82 thus forcing rail and loop sides of suture loop 15 in the portion of suture slots 97 of long applicator 88 where cutter 89 will be pushed to cut sutures 15.

FIG. 8I shows a frontal view of the "rail" side of suture loops 15 coming straight toward the viewer as dots and the loop sides of suture loops 15 as circles wrapped around the "rail" sides. Slip knots 80 are larger than and outside suture slots 97 thus applicator nose 93 pushes the loop side on the "rail" side to vessel wall 28.

FIG. 8J shows the rail and loop sides of suture loops 15 at cross sectional plane h immediately proximal to cross section plane i where they are intertwined in slip knot 80. Also represented at cross sectional plane h is cutter end 89 after it is moved from its position in FIG. 8H but before it is moved far enough to cut sutures 15] and thus only touching rail [and] loop side of any suture loop 15 in suture slot 97 of long applicator 82. This representation of what occurs at cross sectional planes i and h is further described in FIGS. 9 A-E FIG. 9A shows (two examples) of a plurality of cutter ends 89 and cutter pushers 90, located in cutter channels 102. Each cutter channel 102 is a rectangular channel in long applicator 82, about 0.5 mm wide and 1-2 mm in depth, curved on one end in a question mark shape around distal end of snare holder 92 and crossing suture channel 97 at a right angle to push against the opposite side of suture channel 97. Where the question mark shape is at a right angle to suture slots 97, the depth of cutter channel 102 is increased in the direction of short applicator 88 making this portion of cutter channel 102 a groove in long applicator 82. The other end of cutter channel 102 in long applicator 82 extends parallel to suture slot 97, continuing in the proximal direction parallel to longitudinal axis of long applicator 82 and ends near proximal end of long applicator 82. Near the proximal end of long applicator 82 the depth of cutter channel 102 increases in the direction opposite short applicator 88 for a length of about 2-4 mm thus becoming a groove with open side to the outside of long applicator 82. Each cutter pusher 90 is a flexible strip of metal such as spring steel of the same shape but slidably smaller than cutter channel 102, located in cutter channel 102, having cutter end 89 near applicator nose 93, and attached to push knob 91 where the depth of cutter channel 102 increases to the width of long applicator 82 and extending almost to the proximal end of cutter channel 102. Cutter end 89 is the end of cutter pusher 90, sufficient in depth to fill groove in cutter channel 102 around curve that turns to cross suture slot 97 and has a sharp end. Push knob 91 is a bar of high tensile strength metal or polymer that extends across the width of long applicator 82 with a plurality of protrusions that match the locations of and extend into the grooves created where cutter channel 102 increases to the width of long applicator 82 near proximal end. Thus operator pushes knob 91 to move cutter pushers 90 in cutter channels 102 thus causing cutter ends 89 to move in the groove across suture slots 97 in long applicator 82 where sides of suture loops 15 are located. A cross sectional view of push knob 91 with two protrusions as examples of a plurality of protrusions is shown.

FIG. 9B is a detail view of question mark shaped portion of cutter channel 102 before cutter pusher 90 is pushed by push knob 91 being pushed in the distal direction by operator so cutter end 89 has not crossed suture slot 97.

FIG. 9C is a detail view of the question mark shaped portion of cutter channel 102 after push knob 91 is pushed in the distal direction by operator thus causing the sharp cutter end 89 of cutter pusher 90 to cross suture slot 97. thus causing the sharp cutter end 89 of cutter pusher 90 to cross suture slot 97. No suture is shown in suture slot 97 so the detail can be seen but the object is to cut sutures 15 that are located in suture slot 97.

FIG. 9D includes three side views of the protrusion of push knob 91 attached to cutter pusher 90 being pushed to two more distal positions. Cutter end 89 being of greater depth than cutter pusher 90 fills cutter channel where it is a groove that turns to cross suture slot 97 in long applicator 82. Thus when operator pushes push knob 91 in the distal direction cutter 89 moves around the question mark shape of cutter channel 102 shown in this figure by decreasing the portion of cutter 89 that is seen at cross section h, thus representing cutter 89 moving around curve and "disappearing" to the side view.

FIG. 9E shows the three views shown in FIG. 9D but represented in the frontal view at cross section plane h by cutter 89 increasing in size or "reappearing" in the frontal view where cutter 89 is crossing suture slot 97. Two sides of suture loops 15 are represented by dots in suture slot 97 and these disappear when cutter 89 has been moved to its full extent across suture slot 97, representing the cutting of both rail and loop sides of suture loops 15.

FIG. 9F shows a side view of one of a plurality of slip knots 80 snugly fastened to close the opening of slit artery 29 after being pushed on "rail' side of suture loop 15 by applicator nose 93 now located at cross section plane i. Push knob 91 has been pushed to an intermediate position which advances cutter pusher 90 and cutter end 89 in cutter channel 102.

FIG. 9G is a frontal view at cross section h where cutter end 89 advances through cross section plane h and around the curved right angle to be seen in FIG. 9C. Applicator nose 93 surrounded by pinch sleeve 101 which causes slot stoppers 8 to keep both sides of suture loops 15 in line with cutter end 89 which is seen cutting both sides of suture loops 15 between cutter end 89 and opposite wall of suture channel 97, thus showing they have been cut.

FIG. 9H shows push knob 91 pushed to extreme distal position which advances cutter end 89 through cross section plane h and around the curved right angle to be seen in frontal view of applicator nose 93 to have cut both sides of suture loops 15 against opposite wall of suture channel 97.

FIG. 9I shows the remainder of suture loop 15 inside artery side slit 29 permanently tied by slip knot 80 being tightened to a permanent knot and the two sides of suture loops 15 in slip knot 80 have been cut loose from suture loops 15 still inside vessel thus completing the procedure and suture tying component 103 is removed from patient's body.

SUMMARY OF THE INVENTION

A centerboard in the shape of a rectangular board is located between two similar boards of an outboard, all made of high tensile strength metal, carbon fiber, or polymer. Length of centerboard is about 15-30 cm, thickness about 1 mm and width pre-selected to stretch the free edge of the opening to an approximately straight slit, i.e. about 4-15 mm when centerboard is advanced on guidewire through opening into vessel. A plurality of needle pairs are located in a plurality of needle openings spaced 2 mm apart along centerboard width in vessel. Each needle of a pair has a shaft about 0.5 mm in diameter temporarily attached by friction to a needle nose and one end of a plurality of suture loops is attached to each needle nose. One end of each outboard is attached to a blockhead that holds outboards, called legs, apart by the thickness of centerboard. Other end of each outboard leg has a foot projecting a right angle on the distal end which contains tapered needle housings, each with open end located opposite a needle nose located inside vessel wall while needle housing is located outside, making needle housings about 2 mm apart and about 1 mm from the free edge of the slit opening. The needle noses are pushed 1 mm to either side of the free edge by operator pushing a frame located around proximal end of centerboard which pushes longitudinal separator wires with a wedge end between each needle pair to bend needle noses apart by 2 mm across slit. A screw turner on proximal end of outboard has a center channel with female threads that receives a threaded post attached to proximal end of centerboard, thus forcing centerboard and outboard toward each other with sufficient force to push needle noses through calcified vessel walls and into aligned needle housings. Needle nose housings contain housing detents which catch on nose indents to prevent needle noses from being withdrawn. Turning screw turner in the opposite direction breaks temporary friction connections between needle noses and needle shafts and returning frame to original position returns needle shafts to their unbent positions within centerboard thickness. Removing the device from patient's body places the suture ends outside the body and the idea pattern of suture loops in the vessel. Either of two alternative configurations may be used for joining the sutures, a suture tying component which simultaneously ties suture in preformed slip knots, slides them to opening, and cuts ends or a suture clip component that slides a clip to opening that clamps all suture loops together and cut ends.

The invention claimed is:

1. A device for simultaneously placing a plurality of suture loops in an ideal pattern across free edge of an opening in a vessel made by percutaneous entry into the body, when the vessel may be calcified, comprising,
   a. a centerboard in the shape of a flat board having a distal end and a proximal end, and a length therebetween, a width terminating in edges, a thickness between a front face and a back face, and a longitudinal axis being equidistant from the edges and the front face and the back face, and the width being pre-selected to be about one half the circumference of the free edge of the opening in the vessel to be closed, and circumference, the length of the threaded post protruding from the proximal end of the centerboard on the longitudinal axis, and a semicircular suture cove on the distal end of the centerboard in the shape of a slot between the front face and the back face open on the distal end of the centerboard,
   b. a plurality of needle openings each having a proximal end and a distal end with a centerline therebetween, each of the centerlines being parallel to the longitudinal axis, and each of the needle openings being open to the front face and the back face of the centerboard and each of the centerlines being located at about a right angle to an approximately straight line across the width of the centerboard just proximal to the suture cove,
   c. a plurality of needle pairs slidably received within the plurality of needle openings, each having two needles, in two parts, a needle nose and a needle shaft, held together by a temporary connection, wherein the needle shafts are attached to the distal ends of the needle openings and the needle noses point toward the proximal ends of the needle openings and each of the needle noses contains a nose indent,
   d. a plurality of separator wire channels each having a distal end and a proximal end and a length therebetween, wherein the distal ends of the separator wire channels are open to the plurality of needle openings,
   e. a plurality of cross slots, located near the proximal end of the centerboard each of the cross slots having a distal end and a proximal end with an opening therebetween being open to the front face and the back face of the centerboard and the distal end of the cross slots being open to the proximal ends of the plurality of separator wire channels,
   f. a guidewire channel having a proximal end, a distal end and a length therebetween located approximately along the longitudinal axis and having a diameter less than the thickness of the centerboard, and the guidewire channel having a distal port near the distal end of, and open to the back face of the centerboard and a proximal port near the proximal end of, and open to the front face of the centerboard, g. a plurality of separator wires, slidably received within one of the plurality of separator wire channels, and each of the separator wires having a distal end comprising a wedge shape and configured to separate the needle noses when pushed between one of the plurality of a needle pairs, h. a plurality of cross wires slidably received within one of the plurality of in cross slots, and each of the cross wires having two ends and a center point half way between the two ends wherein each of the cross wires is attached at their center point in a right angle to the proximal end of one of the plurality of separator wires, i. a frame for slidably receiving the centerboard therein, the frame having a rectangular box shape and providing finger grips, wherein each of the two ends of the cross wires is attached to the frame, j. a plurality of suture loops stored in the suture cove each of the suture loops having two ends with one of the two ends attached to one of the needle noses of each of the plurality of needle pairs, k. an outboard having a proximal end, a distal end, and a length therebetween, and along the length are two legs attached to a blockhead, each of the legs being of a shape, like a long flat board and like the centerboard but with edges turned in a U-shape toward the other lea wherein the centerboard can slidably be received and the two legs are attached to the blockhead located toward the proximal end of the outboard, and on the distal ends of the legs are foot protuberances having a length, a thickness, and a width, the width being equal to the width of the legs, the thickness being equal to the thickness of the leas and the length extending at a right angle a short distance from the distal ends of the legs making the feet appear turned at a right angle away from the centerboard located between the legs, l. the blockhead having an outside thickness, an outside width and a length, the length extending from the proximal end of the outboard to the outboard legs, the outside thickness being sufficient to overlap the legs, the outside width being about equal to the width of the centerboard near the legs and about equal to the width of the legs near the proximal end of the outboard, and the blockhead has three sets of internal dimensions, the internal dimensions of an unthreaded hole being such as to slidably receive the threaded post and extending from the proximal end of the outboard in the distal direction to a centerboard slot being of dimensions to slidably receive the centerboard and extending distally to a frame slot being of dimensions to slidably receive the frame and extending distally to the legs, m. a plurality of needle nose housings, each being in the shape of a funnel with a narrow end and a wide end, and being of a size for slidably receiving the needle nose and with the narrow end of the funnel in the foot and the wide end of the funnel on the foot at the distal end of the outboard, each of the needle nose housings being located directly opposite one of the needle noses when each of the plurality of needle noses is separated by the wedge ends, and the needle nose housings have housing detents that are located to engage the needle indents, n. a screw turner with the threaded hole in center that self-aligns to engage the threads on the threaded post when the threaded post is in the threaded hole.

2. The device of claim 1 further including, a. the blockhead comprising a split blockhead being of the same material and shape as the blockhead but being separated in two halves along a plane midway between the outboard legs, b. a surround being in the shape of a rectangular box with top and bottom removed and having dimensions to slidably receive the split blockhead, c. a tongue and groove aligned between the split blockhead and the surround, d. one or more spurs in the shape of wire protrusions of stiff material attached to the distal end of the outboard and located on each foot, and protruding at an acute angle that points the one or more spurs on each of the feet toward the front face on one side of, and the back face on the other side of the centerboard located between the legs.

3. The device of claim 1 further including, a. a stopper protruding on each edge of the centerboard and located at a point just proximal to the proximal ends of the plurality of needle openings, b. a keeper being a section of each of the legs that does not have the edges of the leas that are turned in a U-shape toward the other leg and the length of the section of the keeper is equal to the distance the needle noses travel from inside the vessel to be lodged in the needle nose housings.

4. The device of claim 1 wherein, a. a plurality of blunt ends on the distal ends of the plurality of separator wires are blunt, b. a plurality of bridge wires being in the shape of a loop made of a resilient material and having two ends with points mid-way between the two ends being attached to the blunt ends and with each of the two ends attached to one of the needle shafts of each pair of the plurality of needle pairs and the bridge wires being of a length when straight that separates the needle noses so each is of the needle noses is aligned with one of the plurality of needle nose housings.

5. The device of claim 1, wherein, a. a plurality of spring clips made of spring material and each being in the shape of a disc with a circumference and circular open center and having a wide radial cut from the open center to the circumference, b. a plurality of circular slots each being in one of the plurality of needle housings and each being sized and shaped to slidably receive the open center of one of the plurality of spring clips, c. a plurality of circular slots each being in one of the needle noses of the plurality of needle pairs and sized and shaped to slidably receive one of the plurality of spring clips.

6. The device of claim 1 wherein, a. a soft suture cove being made of soft elastic material in a shape like that of the suture cove and attached to the centerboard in the same location as the suture cove, b. the soft suture cove being of the same or a slightly larger size than the suture cove.

7. The device of claim 1, further including, a. a fluid channel having a diameter less than the thickness of the centerboard, and having a proximal end, a distal end and a length therebetween, and being located adjacent the proximal port of the guidewire channel, b. a fluid port proximal on the proximal end of the fluid channel and being located adjacent the proximal port of the guidewire channel,
c. a fluid port distal on the distal end of the fluid channel and being located adjacent the distal port of the guidewire channel.

8. The device of claim 1, further including,
a. a divided fluid channel having a diameter less than the thickness of the centerboard, a proximal end, two distal ends and a single channel that divides into two sections therebetween, the single channel extends adjacent the guidewire channel, then divides into the two sections at a point immediately distal to the proximal end of the guidewire channel and each of the two sections turns at an opposite right angle and runs to the opposite edges of the centerboard,
b. two balloons each one attached to one of the opposite edges of the centerboard
c. two fluid ports edge, each located on the end of one of the two sections of the divided fluid channel and each opening-directly into one of the two balloons.

9. The device of claim 1, wherein,
a plurality of cove walls running parallel to the longitudinal axis of the centerboard and being so spaced within the suture cove as to produce a plurality of suture compartments of equal volume.

* * * * *